United States Patent
Ostler et al.

(10) Patent No.: US 7,320,593 B2
(45) Date of Patent: Jan. 22, 2008

(54) LIGHT EMITTING DIODE LIGHT SOURCE FOR CURING DENTAL COMPOSITES

(75) Inventors: Calvin D. Ostler, Riverton, UT (US); Kevin D. Ostler, South Jordan, UT (US); Bruce R. Walker, West Jordan, UT (US); Marc C. Cimolino, Snohomish, WA (US); Miles F. Elledge, Kirkland, WA (US)

(73) Assignee: TIR Systems Ltd., Burnaby, British Columbia (CA)

( * ) Notice: Subject to any disclaimer, the term of this patent is extended or adjusted under 35 U.S.C. 154(b) by 0 days.

(21) Appl. No.: 09/801,351

(22) Filed: Mar. 7, 2001

(65) Prior Publication Data

US 2001/0046652 A1    Nov. 29, 2001

Related U.S. Application Data

(60) Provisional application No. 60/187,899, filed on Mar. 8, 2000.

(51) Int. Cl.
*A61C 3/00* (2006.01)
(52) U.S. Cl. .......................... 433/29; 362/119
(58) Field of Classification Search ................. 433/29; 362/119, 800
See application file for complete search history.

(56) References Cited

U.S. PATENT DOCUMENTS

| | | |
|---|---|---|
| 3,512,027 A | 5/1970 | Kupsky |
| 3,638,013 A | 1/1972 | Keller |
| 3,712,984 A | 1/1973 | Lienhard |
| 3,733,481 A | 5/1973 | Kuyt |
| 3,868,513 A | 2/1975 | Gonser |
| 3,970,856 A | 7/1976 | Mahaffey et al. |
| 4,048,490 A | 9/1977 | Troue |
| 4,114,274 A | 9/1978 | Jones |
| 4,114,946 A | 9/1978 | Hoffmeister et al. |
| 4,149,086 A | 4/1979 | Nath |
| 4,184,196 A | 1/1980 | Moret et al. |
| 4,185,891 A | 1/1980 | Kaestner |
| 4,186,748 A | 2/1980 | Schlager |
| 4,209,907 A | 7/1980 | Tsukada et al. |
| 4,229,658 A | 10/1980 | Gonser |
| 4,230,453 A | 10/1980 | Reimers |
| 4,233,649 A | 11/1980 | Scheer et al. |
| 4,280,273 A | 7/1981 | Vincent |

(Continued)

FOREIGN PATENT DOCUMENTS

CA    2 190 225    6/1997

(Continued)

OTHER PUBLICATIONS

Web Page: www.dmdcorp.com/appolloelight.htm LED Curing Device 1 page (Mar. 6, 2001).

(Continued)

*Primary Examiner*—John J Wilson
(74) *Attorney, Agent, or Firm*—DLA Piper US LLP

(57) ABSTRACT

Light Emitting Diode Light Sources for Dental Curing are disclosed. Some embodiments of the invention include structures such as Light Emitting Diode Array(s), heat sink, heat dissipation, heat pipe, and control circuitry are disclosed.

20 Claims, 25 Drawing Sheets

U.S. PATENT DOCUMENTS

| | | | |
|---|---|---|---|
| 4,298,806 A | 11/1981 | Herold | |
| 4,337,759 A | 7/1982 | Popovich et al. | |
| 4,346,329 A | 8/1982 | Schmidt | |
| 4,391,588 A | 7/1983 | Matsui | |
| 4,398,885 A | 8/1983 | Loge et al. | |
| 4,412,134 A | 10/1983 | Herold et al. | |
| 4,445,858 A | 5/1984 | Johnson | |
| 4,450,139 A | 5/1984 | Bussiere et al. | |
| 4,610,630 A | 9/1986 | Betush | |
| 4,666,406 A | 5/1987 | Kanca, III | |
| 4,673,353 A | 6/1987 | Nevin | |
| 4,716,296 A | 12/1987 | Bussiere et al. | |
| 4,729,076 A | 3/1988 | Masami et al. | |
| 4,742,432 A | 5/1988 | Thillays et al. | |
| 4,757,381 A | 7/1988 | Cooper et al. | |
| 4,792,692 A | 12/1988 | Herold et al. | |
| 4,810,194 A | 3/1989 | Snedden | |
| 4,822,335 A | 4/1989 | Kawai et al. | |
| 4,826,431 A | 5/1989 | Fujimura et al. | |
| 4,836,782 A | 6/1989 | Gonser | |
| 4,839,566 A | 6/1989 | Herold et al. | |
| 4,888,489 A | 12/1989 | Bryan | |
| 4,893,354 A * | 1/1990 | Janzen et al. | 340/854.7 |
| 4,935,665 A * | 6/1990 | Murata | 313/500 |
| 4,936,808 A | 6/1990 | Lee | |
| 4,948,215 A | 8/1990 | Friedman | |
| 4,963,798 A * | 10/1990 | McDermott | 315/312 |
| 4,999,310 A | 3/1991 | Kim | |
| 5,003,434 A | 3/1991 | Gonser et al. | |
| 5,007,837 A | 4/1991 | Werly | |
| 5,017,140 A | 5/1991 | Ascher | |
| 5,029,957 A | 7/1991 | Hood | |
| 5,070,258 A | 12/1991 | Izumi et al. | |
| 5,115,761 A | 5/1992 | Hood | |
| 5,147,204 A | 9/1992 | Patten et al. | |
| 5,150,016 A | 9/1992 | Sawase et al. | |
| 5,160,200 A | 11/1992 | Cheselske | |
| 5,161,879 A | 11/1992 | McDermott | |
| 5,162,696 A | 11/1992 | Goodrich | |
| 5,169,632 A | 12/1992 | Duell et al. | |
| 5,173,810 A | 12/1992 | Yamakawa | |
| 5,198,678 A | 3/1993 | Oppawsky | |
| 5,201,655 A | 4/1993 | Friedman | |
| 5,233,283 A | 8/1993 | Kennedy | 320/115 |
| 5,242,602 A | 9/1993 | Richardson et al. | |
| 5,265,792 A | 11/1993 | Harrah et al. | |
| 5,268,812 A * | 12/1993 | Conte | 361/698 |
| 5,278,629 A | 1/1994 | Schlager et al. | |
| 5,283,425 A | 2/1994 | Imamura | |
| 5,290,169 A | 3/1994 | Friedman et al. | |
| 5,302,124 A | 4/1994 | Lansing et al. | |
| 5,312,249 A | 5/1994 | Kennedy | |
| 5,316,473 A | 5/1994 | Hare | |
| 5,328,368 A | 7/1994 | Lansing et al. | |
| 5,371,826 A | 12/1994 | Friedman | |
| 5,373,114 A | 12/1994 | Kondo et al. | |
| 5,420,768 A | 5/1995 | Kennedy | 362/119 |
| 5,445,608 A | 8/1995 | Chen et al. | |
| 5,457,611 A | 10/1995 | Verderber | |
| 5,471,129 A | 11/1995 | Mann | |
| 5,474,449 A | 12/1995 | Loge et al. | |
| 5,487,662 A | 1/1996 | Kipke et al. | |
| 5,521,392 A | 5/1996 | Kennedy et al. | |
| 5,530,632 A | 6/1996 | Shikano et al. | |
| 5,535,230 A | 7/1996 | Abe | |
| 5,616,141 A | 4/1997 | Cipolla | |
| 5,617,492 A | 4/1997 | Beach et al. | |
| 5,634,711 A | 6/1997 | Kennedy | 362/119 |
| 5,660,461 A * | 8/1997 | Ignatius et al. | 362/800 |
| 5,664,042 A | 9/1997 | Kennedy | |
| 5,698,866 A | 12/1997 | Doiron et al. | |
| 5,707,139 A | 1/1998 | Haitz | |
| 5,711,665 A | 1/1998 | Adam et al. | |
| 5,747,363 A | 5/1998 | Wei et al. | |
| 5,762,867 A | 6/1998 | D'Silva | |
| 5,800,478 A | 9/1998 | Chen et al. | |
| 5,803,729 A | 9/1998 | Tsimerman | |
| 5,857,767 A | 1/1999 | Hochstein | |
| 5,912,470 A | 6/1999 | Eibofner et al. | |
| 5,928,220 A | 7/1999 | Shimoji | |
| 5,975,895 A | 11/1999 | Sullivan | |
| 6,008,264 A | 12/1999 | Ostler et al. | |
| 6,033,223 A | 3/2000 | Narusawa et al. | |
| 6,045,240 A * | 4/2000 | Hochstein | 362/294 |
| 6,102,696 A | 8/2000 | Oswalder | 433/29 |
| 6,159,005 A | 12/2000 | Herold et al. | |
| 6,171,331 B1 | 1/2001 | Bagraev et al. | |
| 6,200,134 B1 * | 3/2001 | Kovac et al. | 433/29 |
| 6,331,111 B1 * | 12/2001 | Cao | 433/29 |
| 2001/0007739 A1 | 7/2001 | Eibofner et al. | |

FOREIGN PATENT DOCUMENTS

| | | |
|---|---|---|
| DE | 295 11 927 U1 | 2/1997 |
| DE | 100 10 638 A1 | 3/2000 |
| EP | 0 116 405 A1 | 8/1984 |
| EP | 0 266 038 B1 | 10/1991 |
| EP | 0 320 080 B1 | 8/1993 |
| EP | 0 672 435 A1 | 9/1995 |
| EP | 0 678 282 A2 | 10/1995 |
| EP | 0 755 662 A1 | 1/1997 |
| EP | 0 780 103 A2 | 6/1997 |
| EP | 0 879 582 A2 | 11/1998 |
| EP | 1 031 326 A1 | 8/2000 |
| EP | 1 090 607 A1 | 4/2001 |
| EP | 1 090 608 A1 | 4/2001 |
| EP | 1 112 721 A1 | 7/2001 |
| EP | 1 138 276 A1 | 10/2001 |
| GB | 2 212 010 A | 7/1989 |
| GB | 2 218 636 A | 11/1989 |
| GB | 2 329 756 A | 3/1999 |
| JP | 51-42607 | 4/1976 |
| JP | 6285508 A | 10/1994 |
| JP | 7163863 A | 6/1995 |
| JP | 8141001 A | 6/1996 |
| JP | 8194786 A | 7/1997 |
| WO | WO 83/01311 A1 | 4/1983 |
| WO | WO 84/04463 A1 | 11/1984 |
| WO | WO 92/02275 A1 | 2/1992 |
| WO | WO 93/09847 A1 | 5/1993 |
| WO | WO 93/21842 A1 | 11/1993 |
| WO | WO 95/07731 A1 | 3/1995 |
| WO | WO 95/19810 A1 | 7/1995 |
| WO | WO 95/26217 A1 | 10/1995 |
| WO | WO 97/36552 A1 | 10/1997 |
| WO | WO 97/37722 A1 | 10/1997 |
| WO | WO 97/46279 A1 | 12/1997 |
| WO | WO 97/46280 A1 | 12/1997 |
| WO | WO 98/03131 A1 | 1/1998 |
| WO | WO 98/04317 A1 | 2/1998 |
| WO | WO 99/09071 A1 | 2/1999 |
| WO | WO 99/11324 A1 | 3/1999 |
| WO | WO 99/16136 | 4/1999 |
| WO | WO 99/16136 | 4/1999 |
| WO | WO 99/20346 A1 | 4/1999 |
| WO | WO 99/35995 A1 | 7/1999 |
| WO | WO 00/01464 A2 | 1/2000 |
| WO | WO 00/02491 A1 | 1/2000 |
| WO | WO 00/13608 A1 | 3/2000 |
| WO | WO 00/15296 A1 | 3/2000 |
| WO | WO 00/41726 A2 | 7/2000 |
| WO | WO 00/41767 A1 | 7/2000 |
| WO | WO 00/41768 A1 | 7/2000 |
| WO | WO 00/43067 A1 | 7/2000 |

| | | |
|---|---|---|
| WO | WO 00/43068 A1 | 7/2000 |
| WO | WO 00/43069 A1 | 7/2000 |
| WO | WO 00/45733 A1 | 8/2000 |
| WO | WO 00/67048 A2 | 11/2000 |
| WO | WO 00/67660 A1 | 11/2000 |
| WO | WO 01/01118 A1 | 1/2001 |
| WO | WO 01/03770 A1 | 1/2001 |
| WO | WO 01/14012 A1 | 3/2001 |
| WO | WO 01/19280 A1 | 3/2001 |
| WO | WO 01/24724 A1 | 4/2001 |
| WO | WO 01/54770 A1 | 8/2001 |
| WO | WO 01/60280 A1 | 8/2001 |
| WO | WO 01/64129 A1 | 9/2001 |
| WO | WO 01/68035 A2 | 9/2001 |
| WO | WO 01/69691 A1 | 9/2001 |

OTHER PUBLICATIONS

Web Page: www.luma-lite.com.html.lumacare.html LED Curing Device 1 page (Mar. 6, 2001).

LumiLeds Lighting LLC, *Lumen Maintenance of White Luxeon™ Power Light Sources*, Application Brief AB07, LumiLeds Lighting, US LLC, Mar. 2006.

LumiLeds Lighting LLC, *Application Breif AB20-5, replaces AN1149-5, Secondary Optics Design Considerations for Super Flux LEDs*, Copyright © 2002 LumiLeds Lighting, Publication No. AB20-5.

Burgess, John et al., *An Evaluation of Four Light-curing Units Comparing Soft and Hard Curing*, Pract. Periodont. Aesthet. Dent. 11(1), 125-132, 1999.

Davidson-Kaban, Saliha S. et al., *The Effect of Curing Light Variations on Bulk Curing and Wall-toWall Quality of Two types and Various Shades of Resin Composites*, Dent. Mater. 13, 344-352, Nov. 27, 2003.

Feitzer, A.J. et al., *Influence of Light Intensity on Polymerization Shrinkage and Integrity of Restoration-cavity Interface*, Eur. J. Oral Sciences, 103, 322-326, 1995.

Koran, Peter et al., *Effect of Sequential Versus Continuous Irradiation of a Light-Cured Resin Composite on Shrinkage, Viscosity, Adhesion, and Degree of Polymerization*, Am. J. of Dentistry, 11, No. 1, 17-22, 1998.

Mayes, Joe H., *Curing Lights; An Overview*, Ormco, vol. 9, No. 2, 2000, p. 15-17.

Mehl, A. et al., *Physical Properties and Gap Formation of Light-Cured Composites With and Without 'Softstart-Polymerization'*, J of Dentisity, 25, 321-330, 1997.

Sakaguchi, Ronald L. et al., *Recuded Light Energy Density Decreases Post-Gel Contraction While Maintaining Degree of Conversion in Composites*, J. of Dentistry, 26, 695-700, 1998.

Schlager, Kenneth J., et al., *An LED-Array Light Source for Medical Therapy*, SPIE vol. 1892, Medical Lasers and Systems II, p. 26-35, 1993.

Tarle, Z. et al., *The Effect of the Pohotopolymerization Method on the Quality of Composite Resin Samples*, J. of Oral Rehab, 25, 436-442, 1998.

Hiromasa, Kato, Relationship Between Velocity of Polymerization and Adaptation to Dentin Cavity Wall of Light-Cured Composite, Dental Materials Journal, 6(1), 32-37, 1987.

* cited by examiner

TOP VIEW

SIDE VIEW

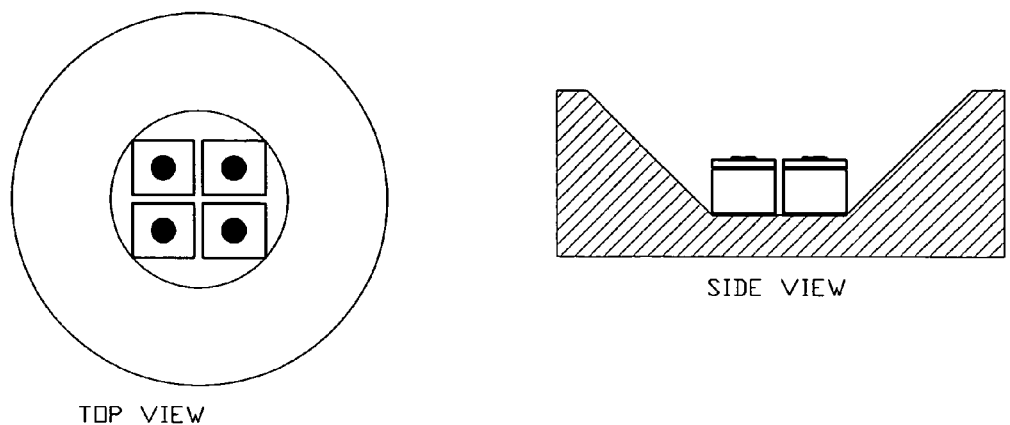
TOP VIEW    SIDE VIEW
FIGURE 900
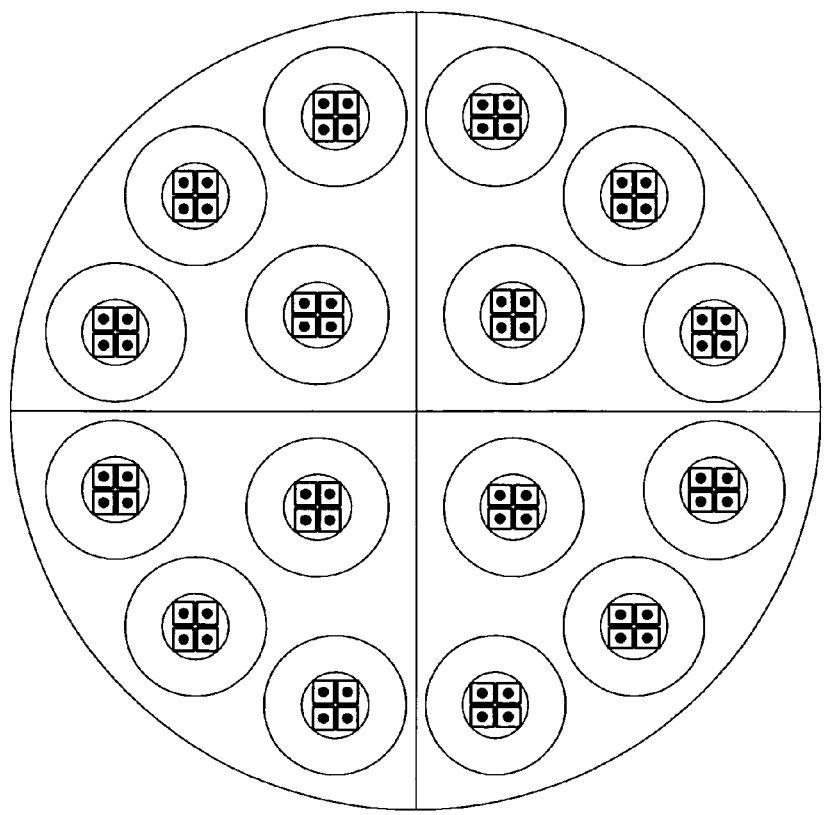
FIGURE 1000

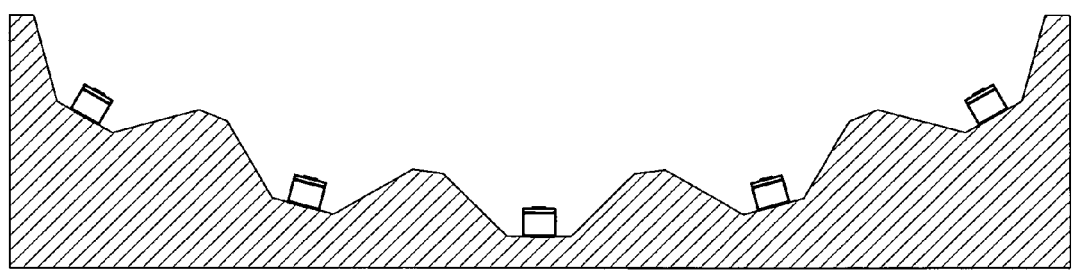
FIGURE 1100

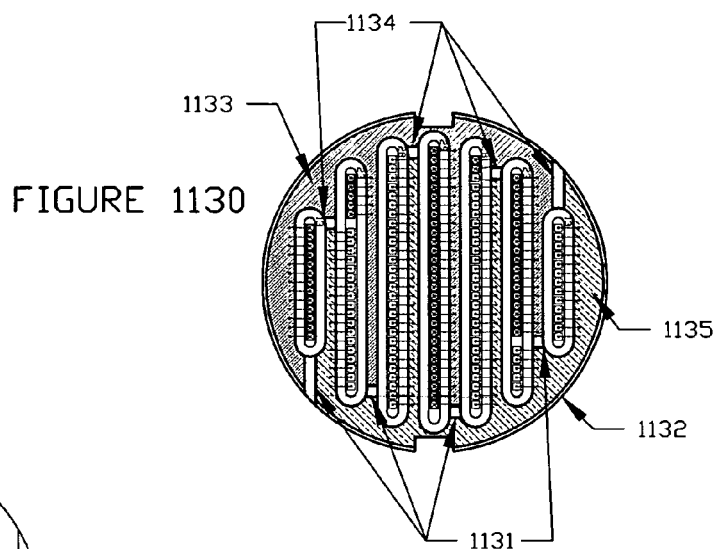
FIGURE 1130
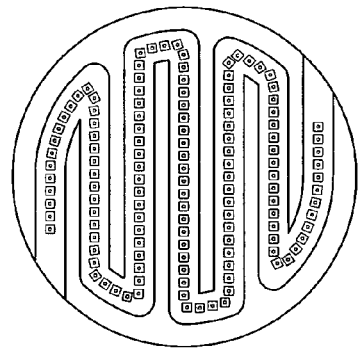
FIGURE 1105
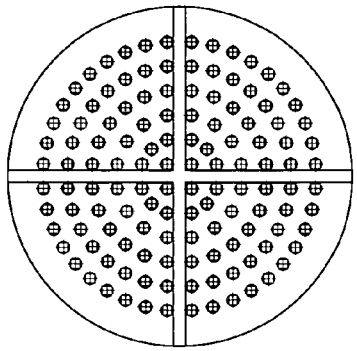
FIGURE 1120
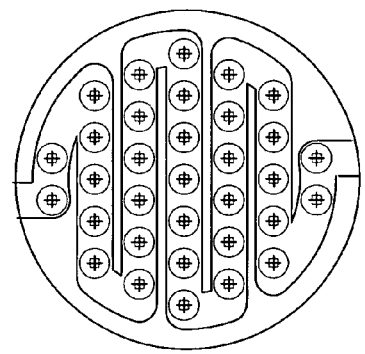
FIGURE 1110
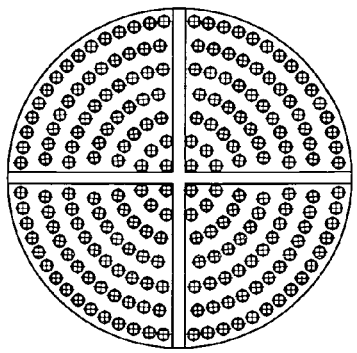
FIGURE 1115

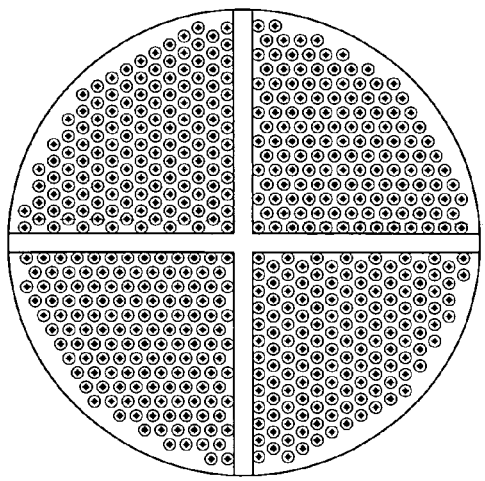
FIGURE 1150
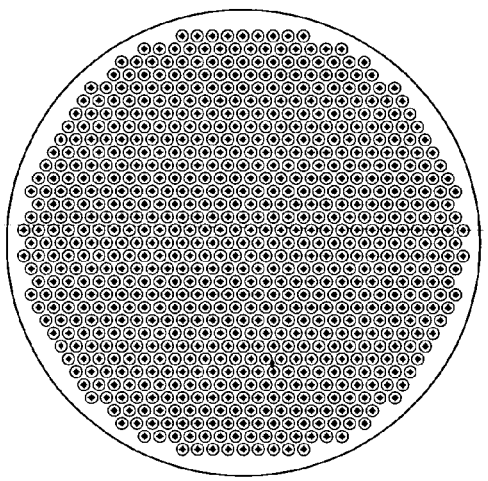
FIGURE 1165
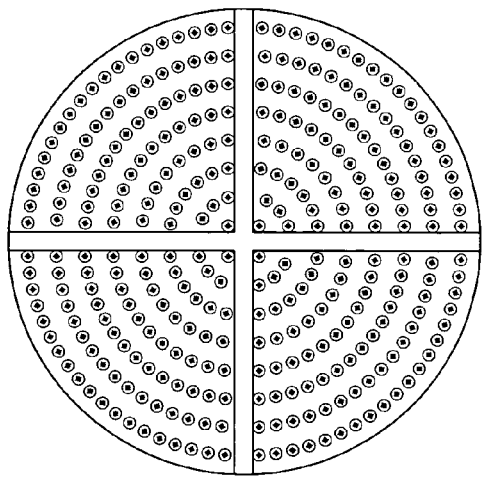
FIGURE 1155
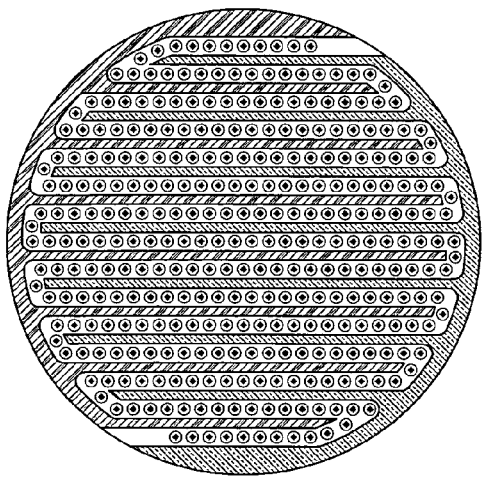
FIGURE 1160

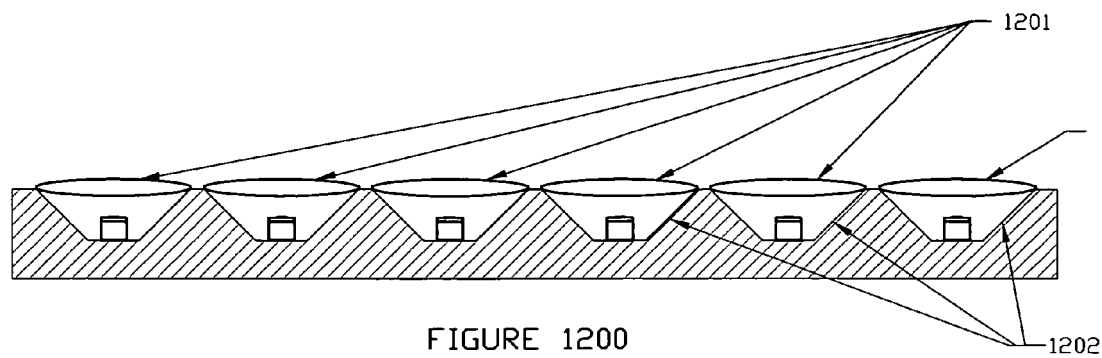
FIGURE 1200
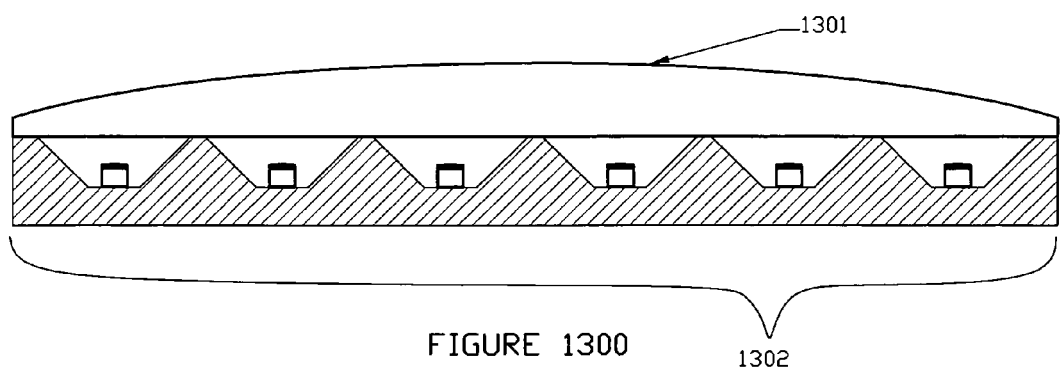
FIGURE 1300
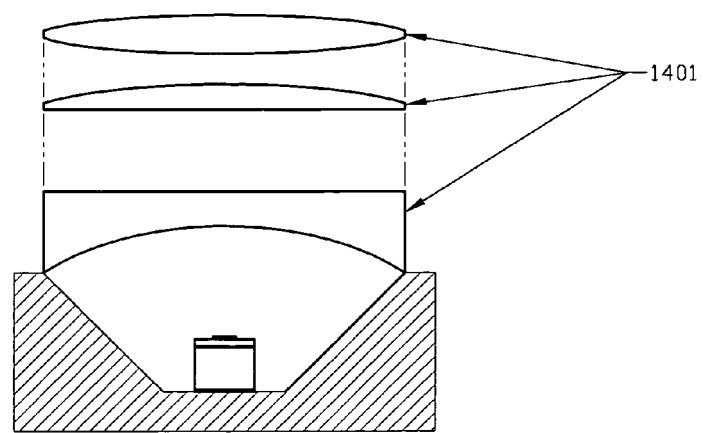
FIGURE 1400

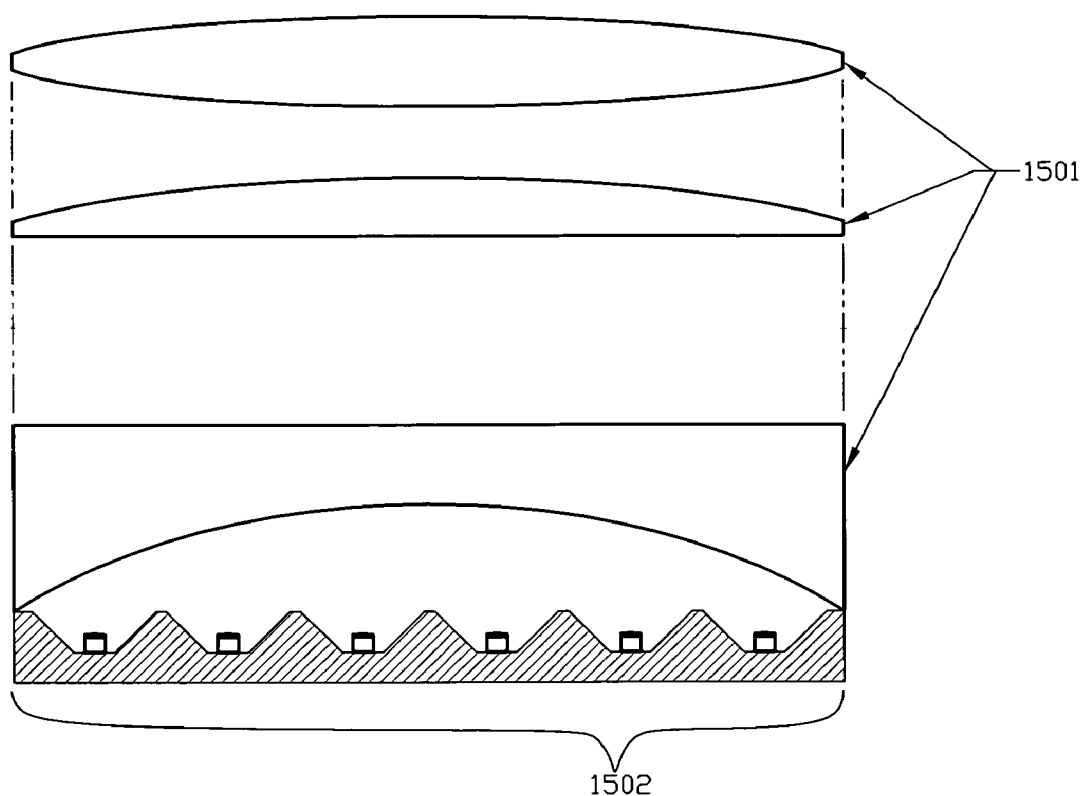
FIGURE 1500
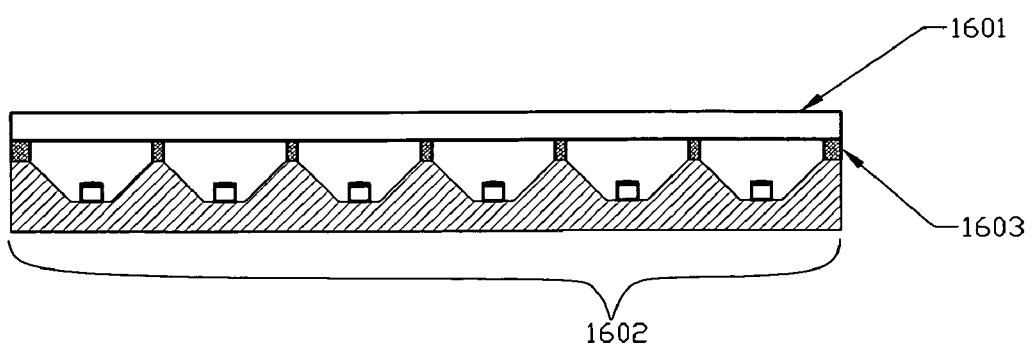
FIGURE 1600

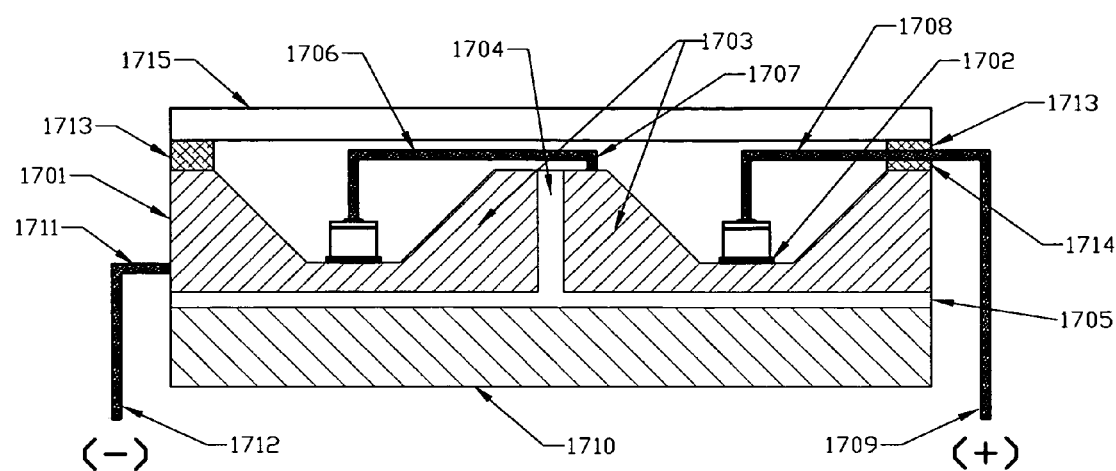
FIGURE 1750
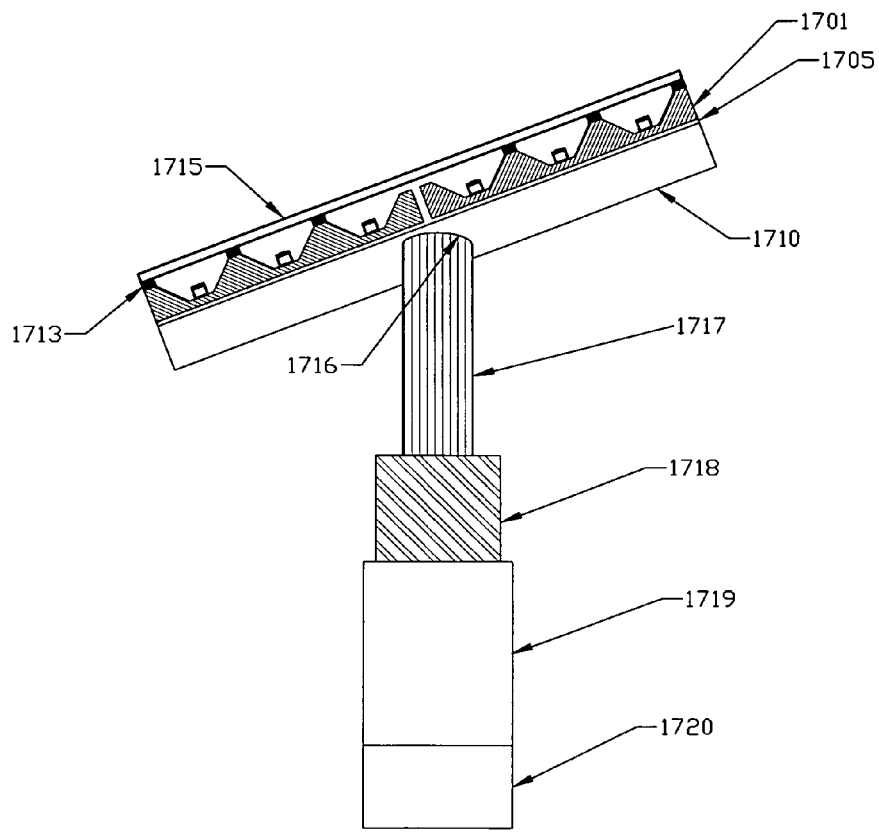
FIGURE 1700

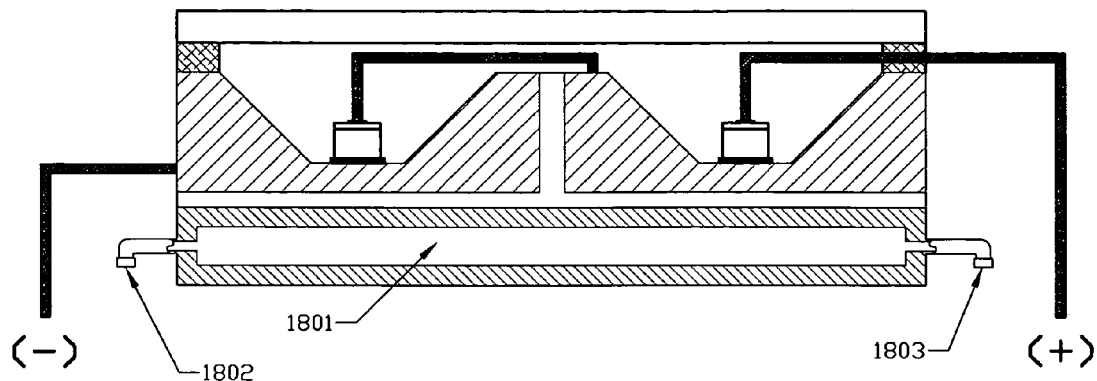
FIGURE 1800
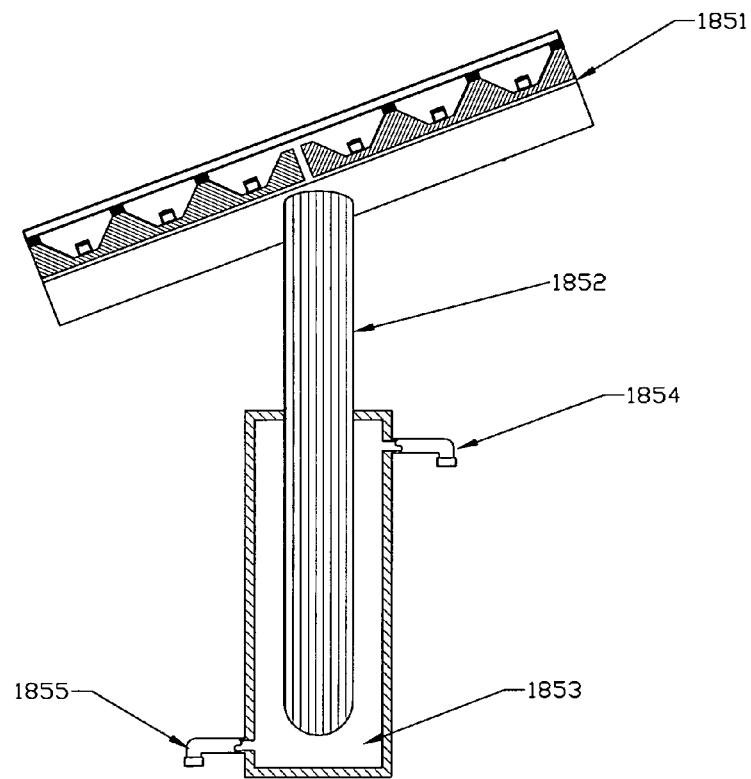
FIGURE 1850

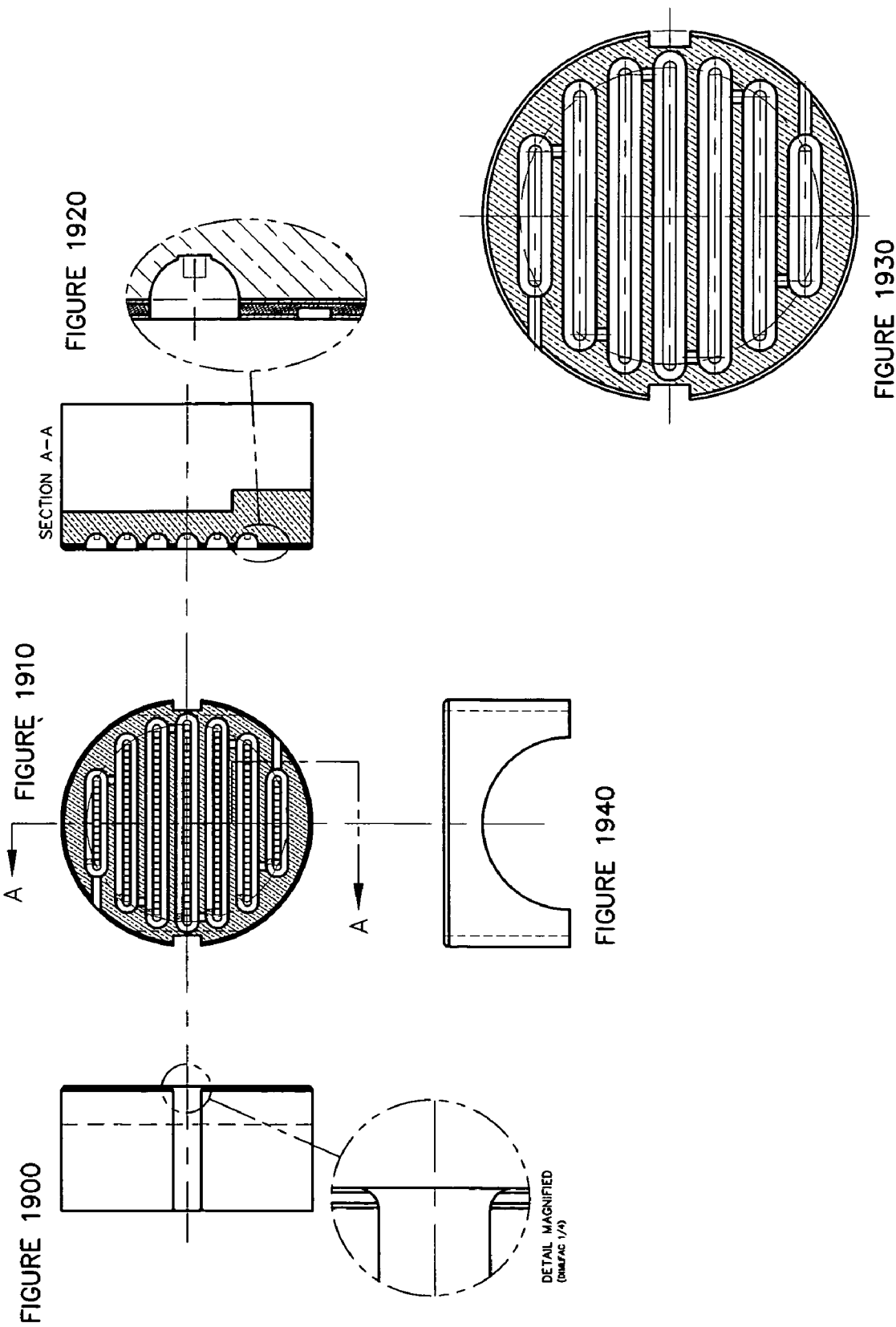

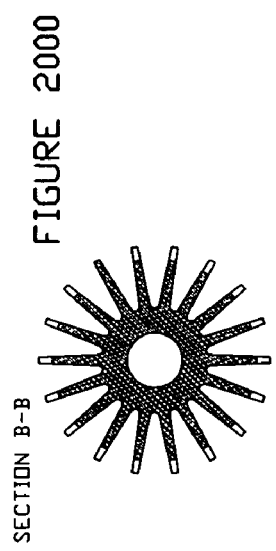
FIGURE 2000
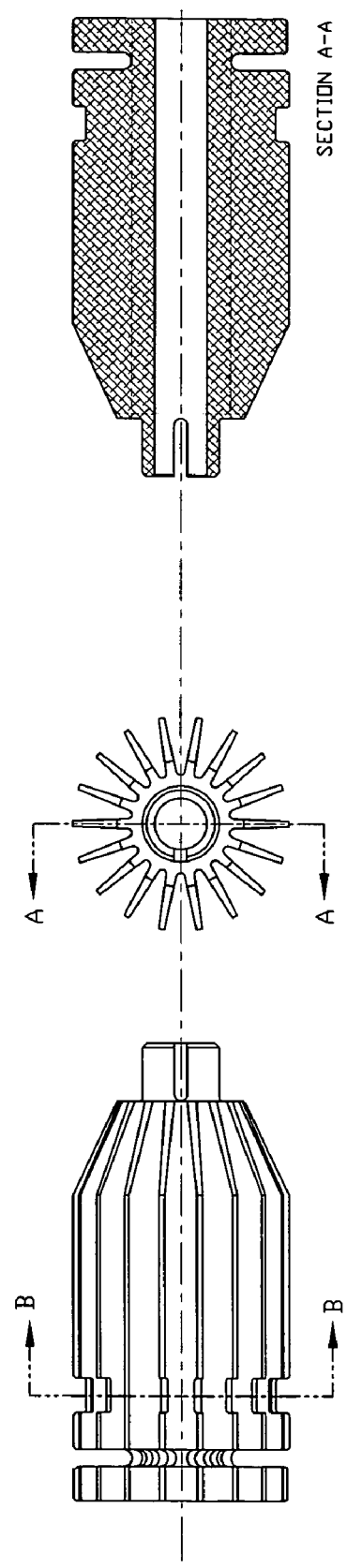
FIGURE 2030
FIGURE 2020
FIGURE 2010

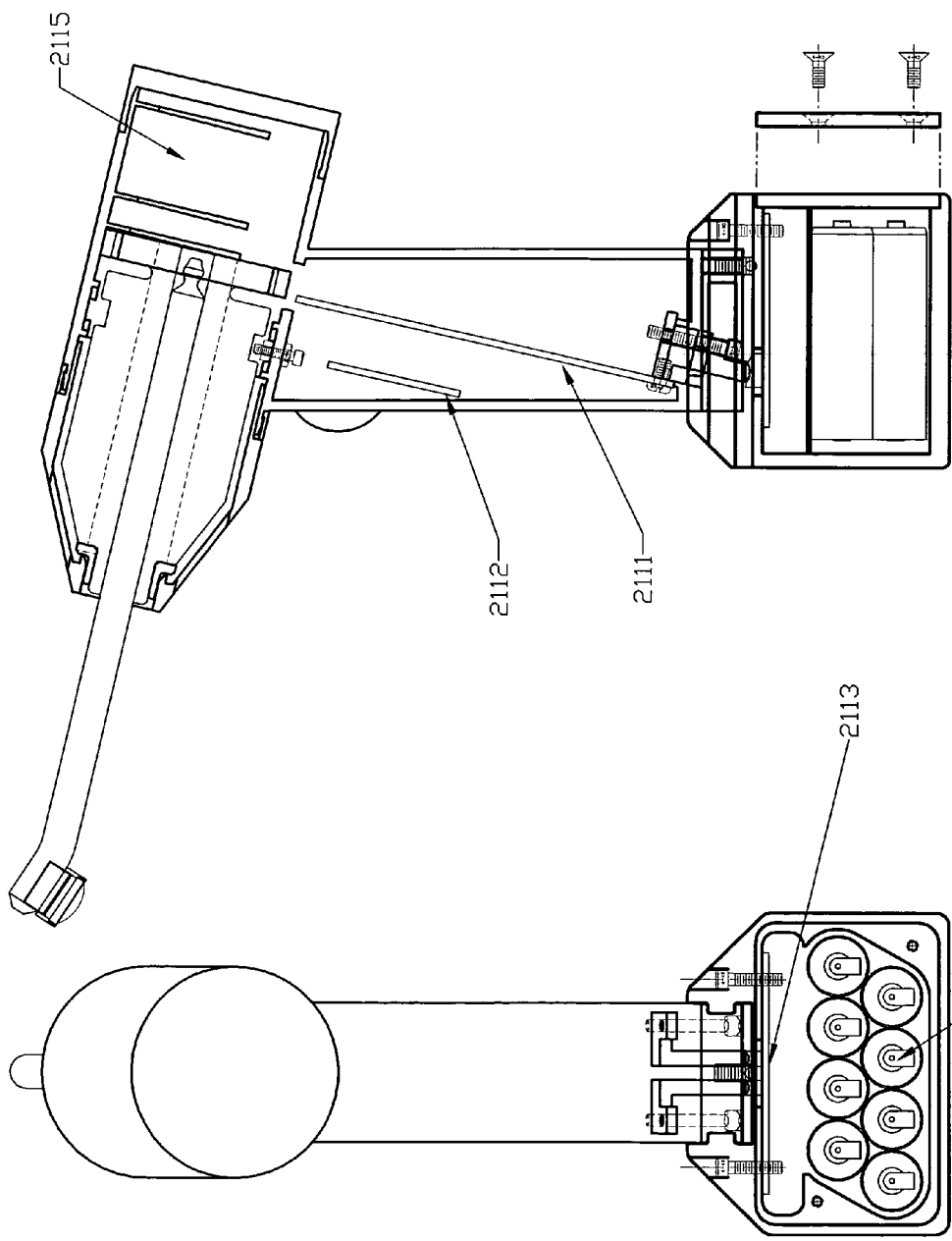

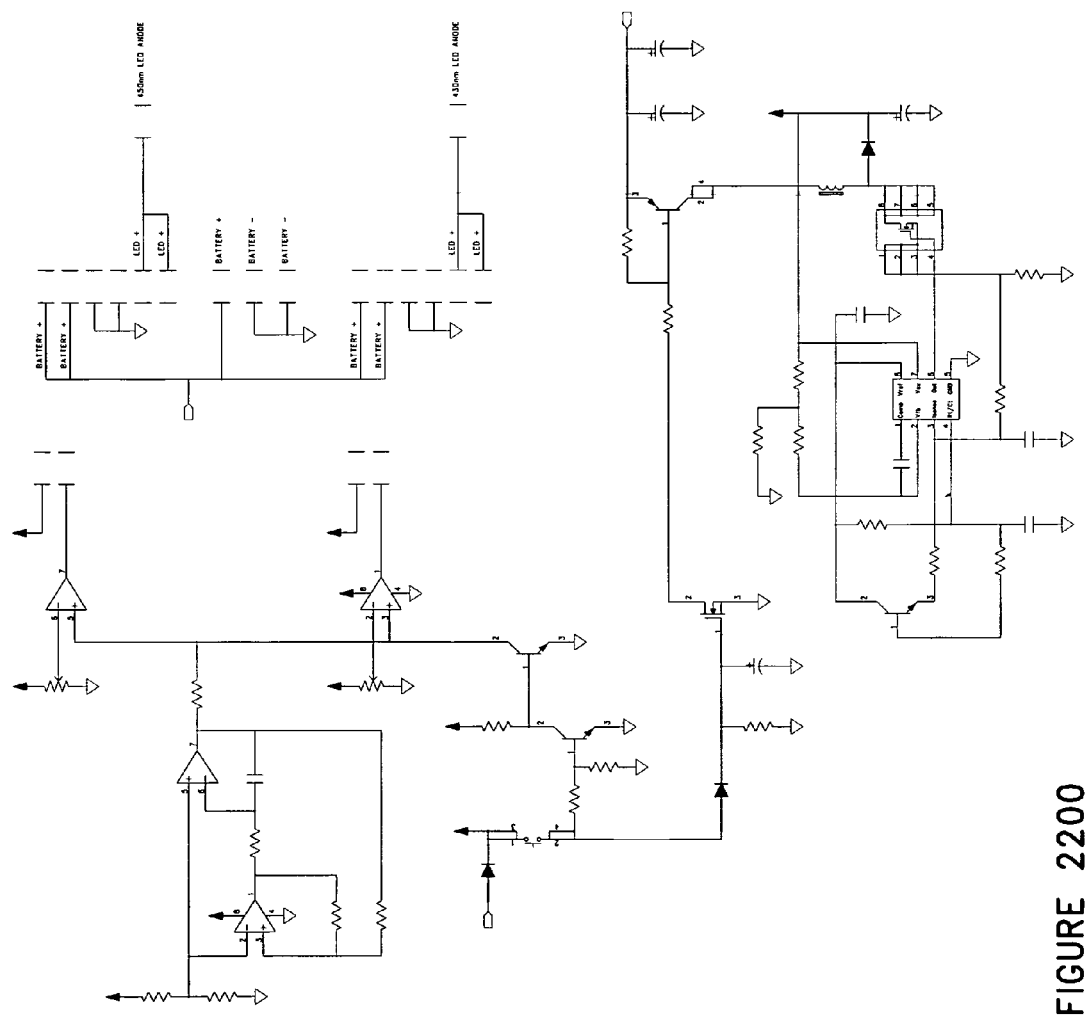
FIGURE 2200

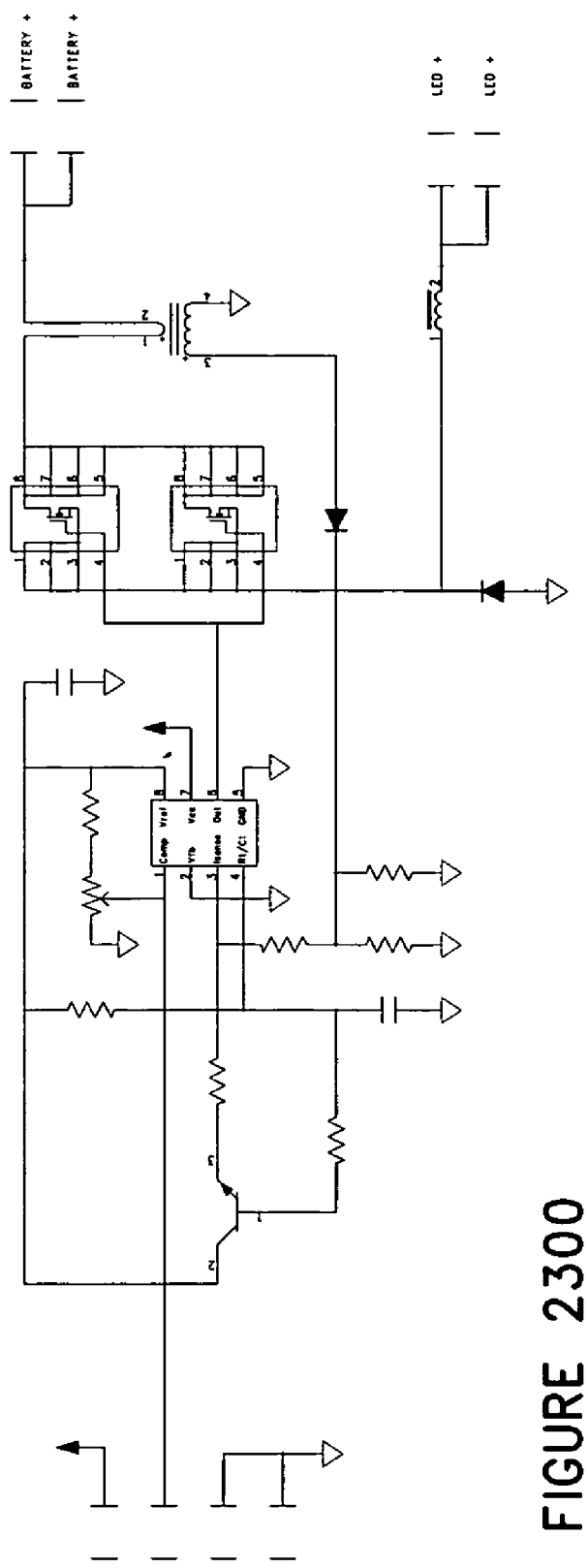
FIGURE 2300

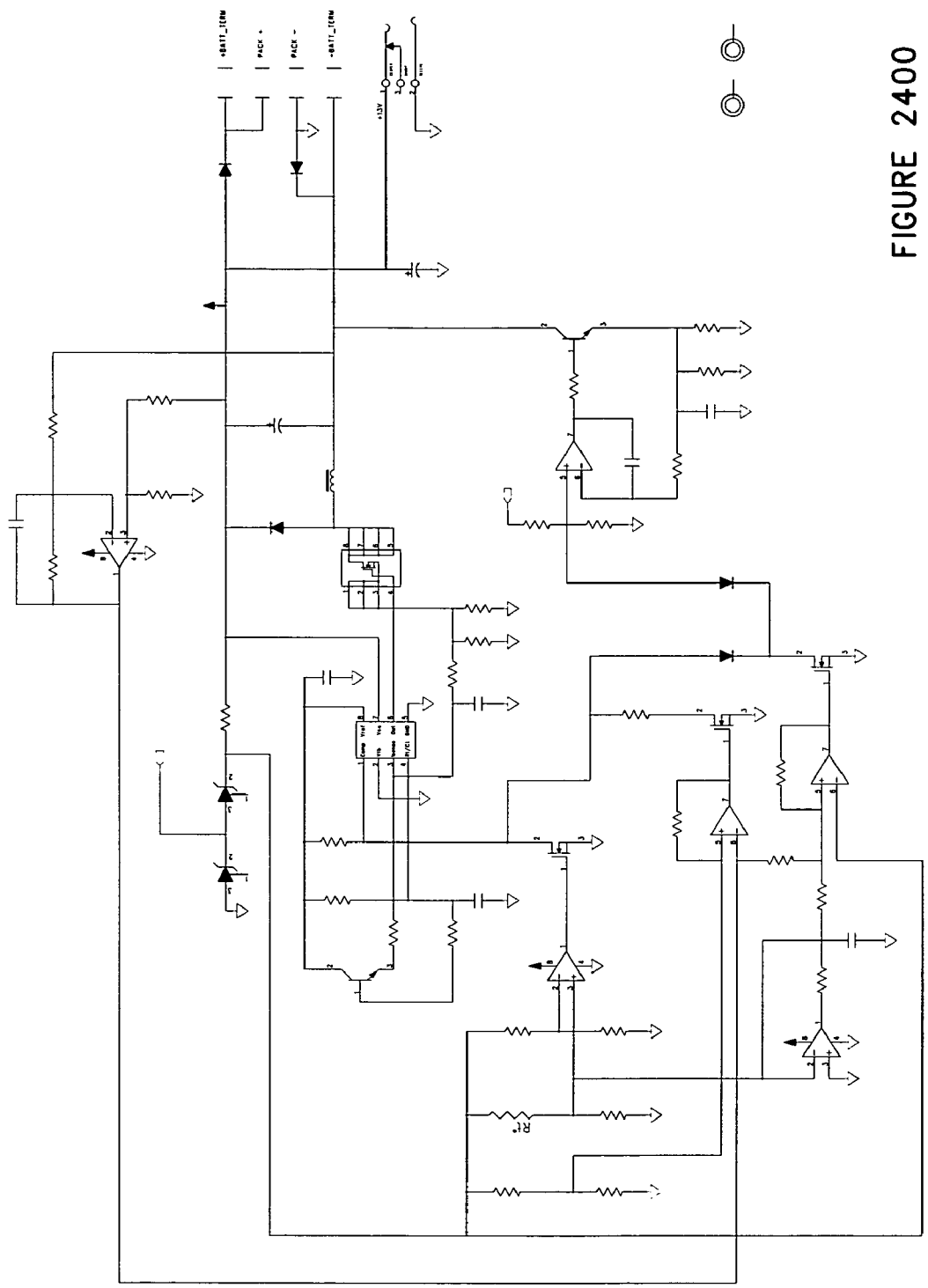
FIGURE 2400

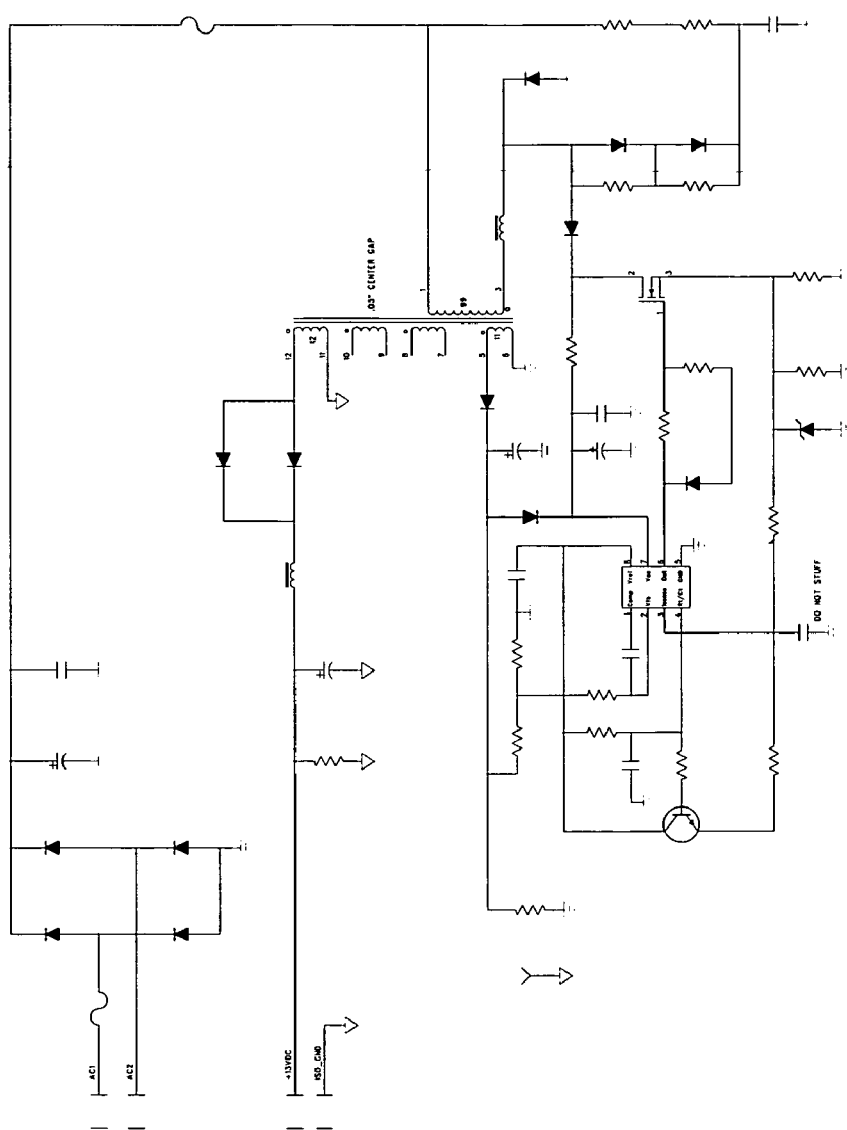
FIGURE 2500

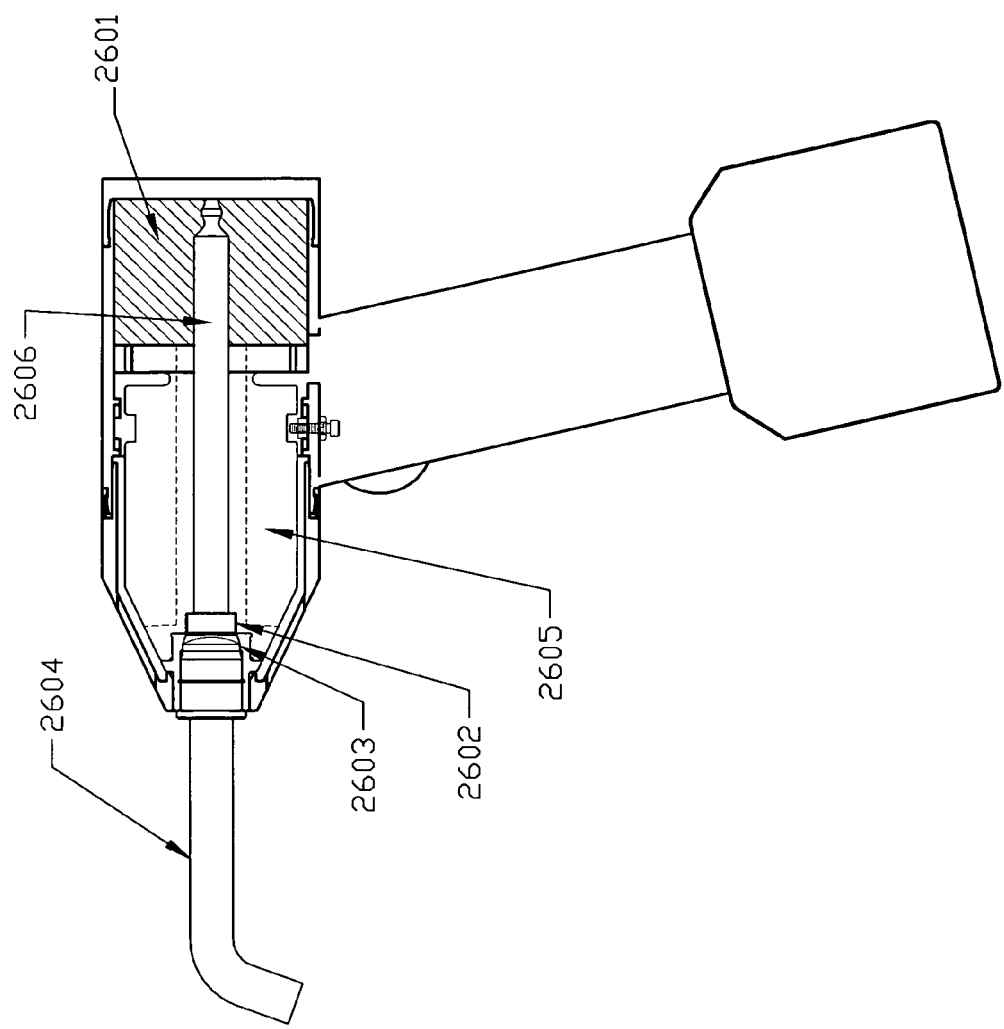
FIGURE 2600

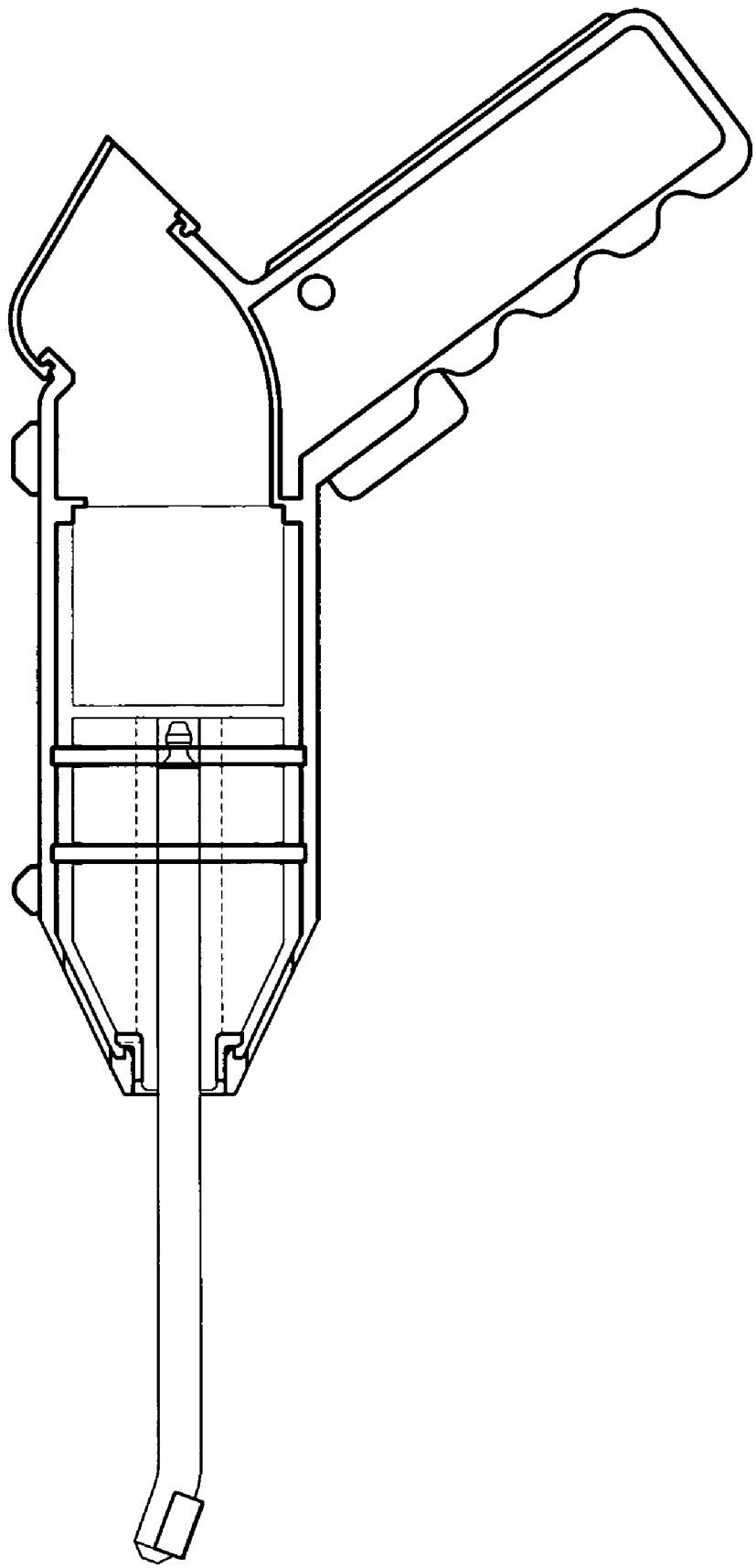
FIGURE 2700

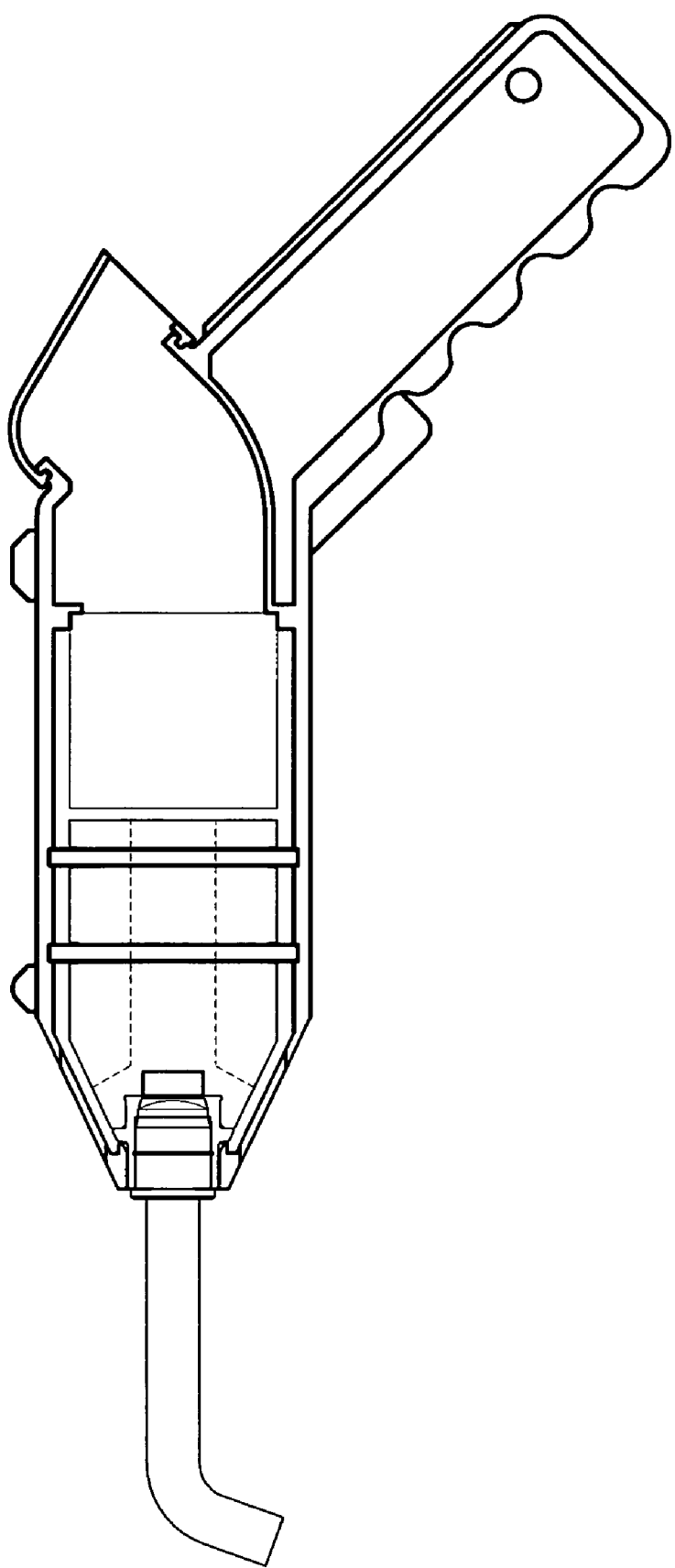
FIGURE 2800

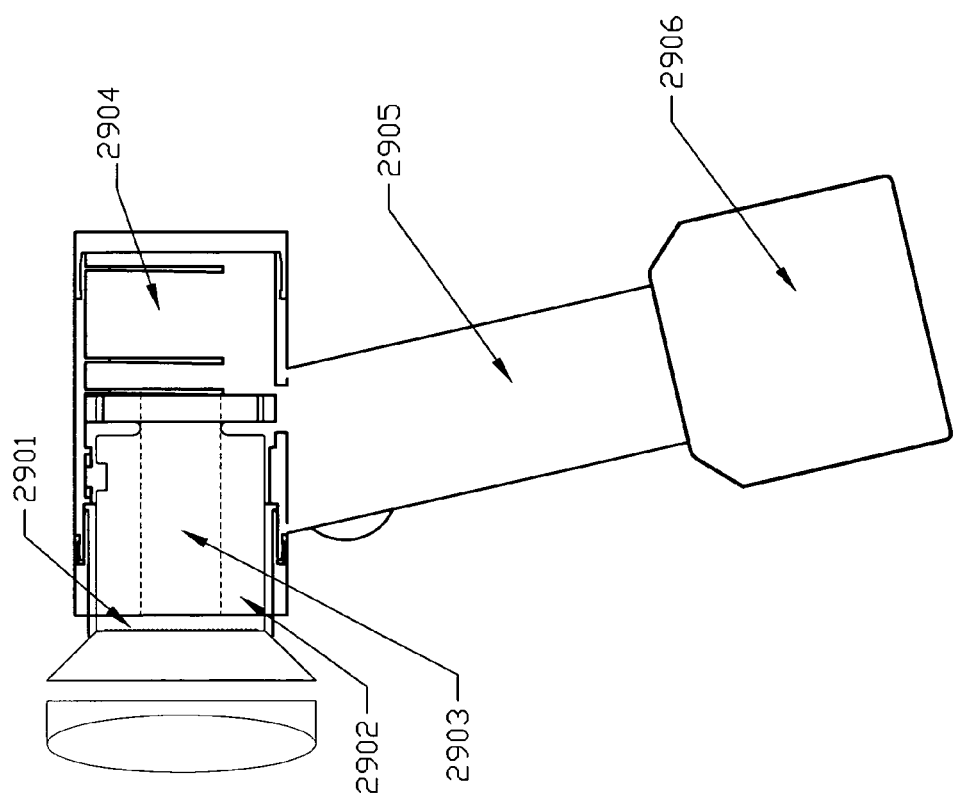
FIGURE 2900

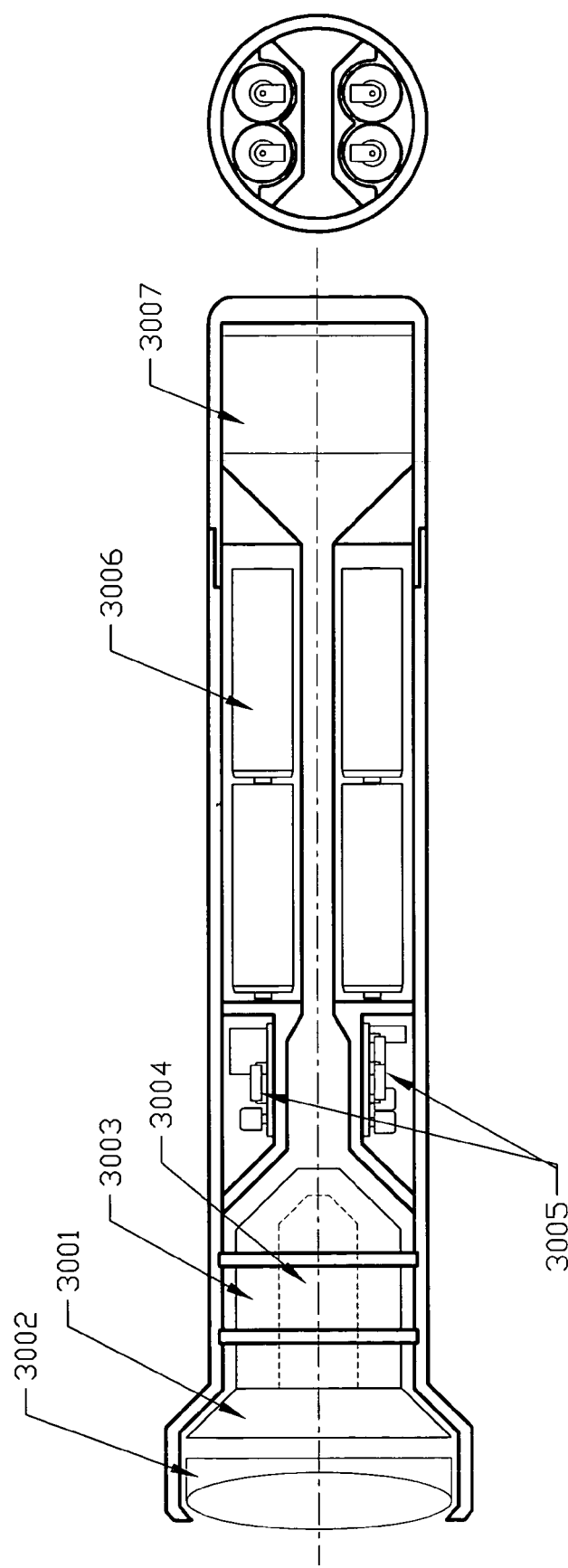
FIGURE 3000

LIGHT EMITTING DIODE LIGHT SOURCE FOR CURING DENTAL COMPOSITES

PRIORITY:

Priority is hereby claimed to U.S. Provisional Patent Application Ser. No. 60/187,899 filed on Mar. 8, 2000.

VI. BACKGROUND OF THE INVENTION

This invention relates to the use of Light Emitting Diodes (LEDs) as a light source for curing dental composite materials.

VII. THE BACKGROUND ART

Light Emitting Diodes produce a narrow bandwidth of light output wavelengths. Because dental composite materials require specific and narrow bandwidths of light to polymerize correctly attempts have been made to utilize Light Emitting Diodes in dental curing lights. Furthermore, Light Emitting Diodes produce no infrared energy and, thereby, produce no heat that can be radiated to the patient. Unfortunately, current Light Emitting Diodes, that produce the blue wavelengths requisite to cure dental composites, have a low power output (on the order of 5 milliwatts total blue light output). Furthermore, it is only possible, with current technology, to deliver about 30-40% of the light produced to the dental material. A threshold of about 100 milliwatts is necessary to begin the curing process on most dental composites. Therefore, a number of diodes must be used to achieve output powers that will cure the dental composites. Further complicating the technology is the low overall efficiency of the Light Emitting Diodes; they are about 6% efficient. Meaning that in order to receive 5 milliwatts in optical energy one must expend 80 milliwatts of electrical energy. The difference in energy in versus optical energy out is dissipated in the form of heat. For every 5 milliwatts of optical energy produced a curing device must dissipate 75 milliwatts worth of heat generated within the Light Emitting Diode.

LumaLite, Inc. of Spring Valley Calif. has invented a Light Emitting Diode curing light, brand named the Luma-Cure. This light is comprised of 7 Light Emitting Diodes which produce, in ideal circumstances, 35 milliwatts of optical curing energy which is insufficient to hit the threshold of 100 milliwatts and as a result does not cure dental composites. Dental/Medical Diagnostic Systems, Inc. of Wookland Hills, Calif. has invented a Light Emitting Diode curing light that contains over 60 Light Emitting Diodes, however, the device is incapable of dissipating the 4500 milliwatts of thermal energy produced for more than a few seconds, therefore, the device has been found in dentistry to be of little clinical value. Inventor John Kennedy has invented several designs (U.S. Pat. Nos.: 5,420,768, / 5,420, 768 / 5,233,283) of Light Emitting Diode dental curing lights. None of the designs adequately manage the heat produced by the Light Emitting Diodes and, subsequently, no working models have been introduced to commerce. Inventor J. Martin Osterwalder has invented a Light Emitting Diode dental curing light (U.S. Pat. No.: 6,102,696) which contains insufficient numbers of Light Emitting Diodes to hit the dental composite curing threshold and has no provision for dissipating the heat produced by the Light Emitting Diodes, subsequently, no working models have been introduced to commerce utilizing the design.

VIII. OBJECTS OF THE INVENTION

It is an object of the invention to provide a Light Emitting Diode (LED) light source for the curing of dental composite materials that has sufficient power to cure the material and adequate heat management structures to avoid heat damage to the curing light itself and the patient.

Additional objects, features and advantages of the invention will become apparent to persons of ordinary skill in the art upon reading the specification in light of the attached drawings.

IX. BRIEF DESCRIPTION OF THE DRAWINGS

Figure 625:
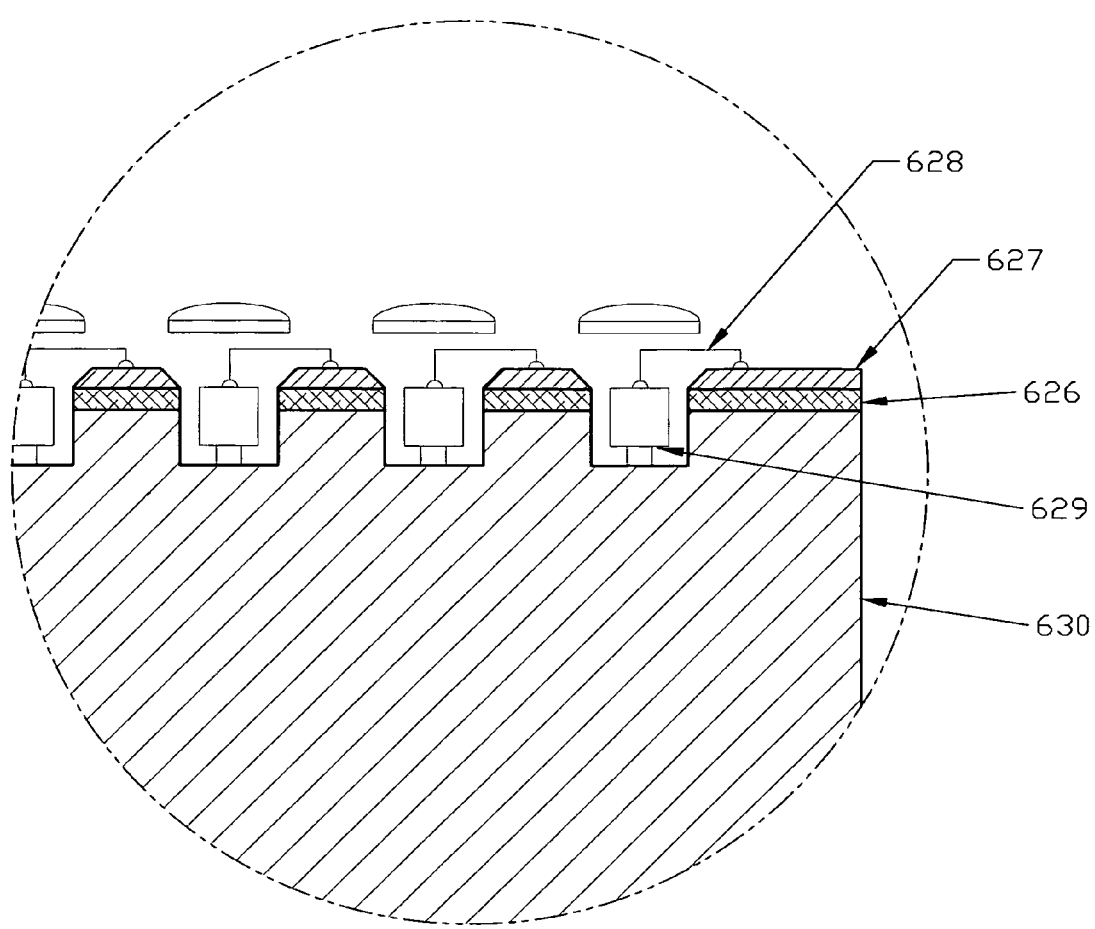

FIG. 625 depicts a Light Emitting Diode array set in a square cup with an angled reflective surface at the top of the cup. Additional focusing/columniation provided by an array of lenses. Electrical connections of the Light Emitting Diodes is also depicted.

Figure 650:
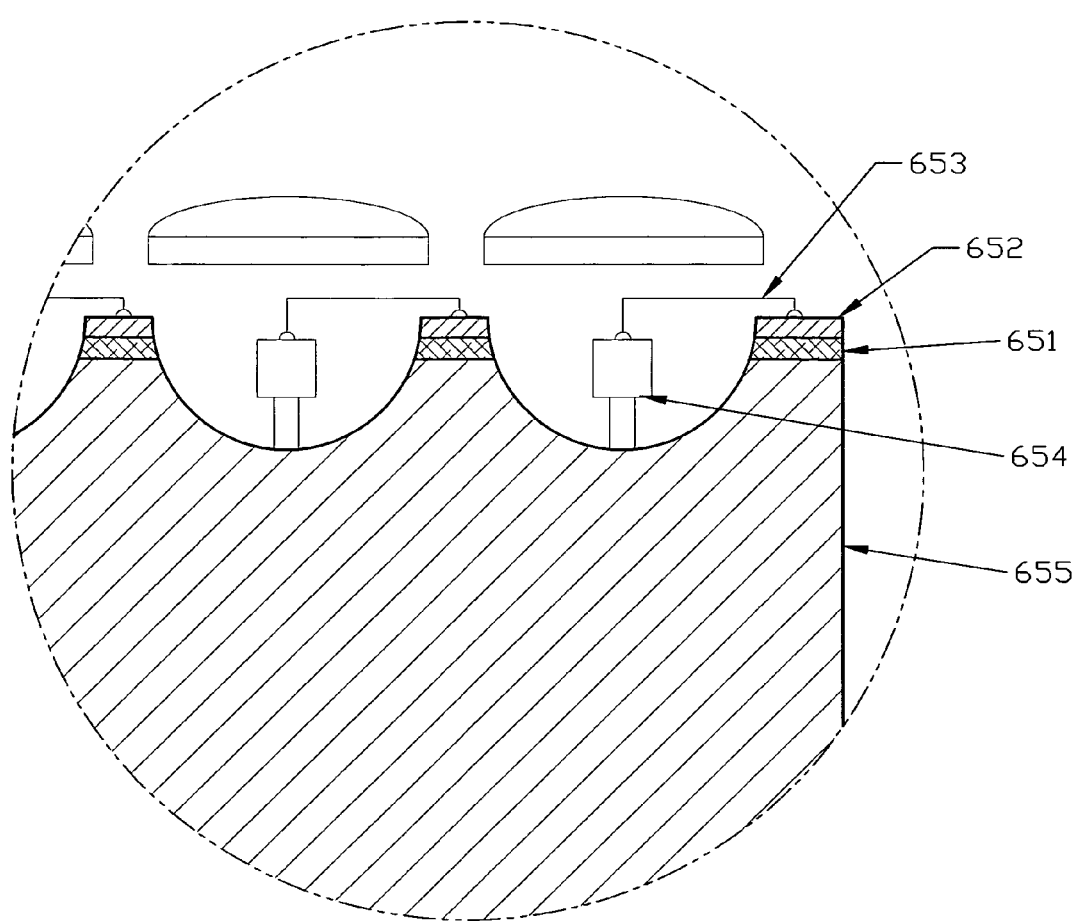

FIG. 650 depicts a Light Emitting Diode array placed in curved cups with further focusing/columniation provided by an array of lenses. Electrical connection of the Light Emitting Diodes is also depicted.

Figure 675:
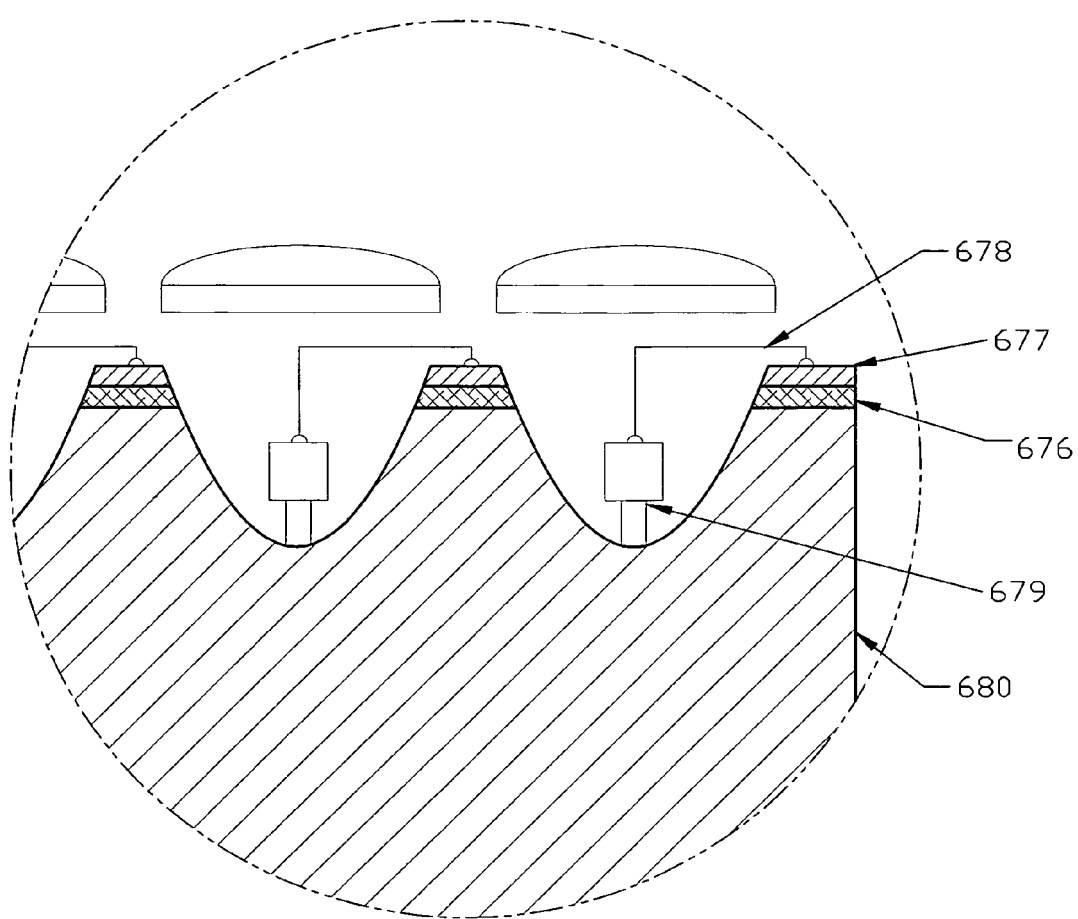

FIG. 675 depicts a Light Emitting Diode array placed in elliptical curved cups with further focusing/columniation provided by an array of lenses. Electrical connection of the Light Emitting Diodes is also depicted.

FIG. 900 depicts an array of 4 Light Emitting Diodes being placed in a single cup with angled reflective walls.

FIG. 1000 depicts an array of 12 cups (angled or curved wall) with 4 Light Emitting Diodes in each cup. Further depicted is the electrical isolation of the cup arrays; they are electrically isolated in groups of 4 cups.

FIG. 1100 depicts an array of Light Emitting Diodes placed in angle walled cups which are arranged in a curved shape.

FIG. 1105 depicts an array of Light Emitting Diodes placed in angled reflective walled or curved reflective walled trenches.

FIG. 1110 depicts an array of Light Emitting Diodes that are placed in cups as well as trenches.

FIG. 1115 depicts a large array of Light Emitting Diodes that are placed in cups (singularly or in groups) which are electrically isolated from each other in quarters.

FIG. 1120 depicts a less dense array of Light Emitting Diodes, in cups and electrically isolated from each other in quarters.

FIG. 1130 depicts an array of Light Emitting Diodes comprised of 2 separate types of Light Emitting Diodes which are placed in angle or curved reflective wall trenches. Electrical isolation of the two different types of diodes as well as their electrical connection is also depicted.

FIG. 1150 depicts a closely compacted Light Emitting Diode array placed in individual angled or curved reflective wall cups. Quartered electrical isolation is also depicted.

FIG. 1155 depicts a less tightly compacted array of Light Emitting Diodes placed in single angled or curved reflective wall cups. Quartered electrical isolation is also depicted.

FIG. 1160 depicts a Light Emitting Diode array placed in angled or curved reflective wall trenches. Halved electrical isolation is also depicted.

FIG. 1165 depicts a tightly compacted array of Light Emitting Diodes placed in single angled or curved reflective wall cups with no electrical isolation.

FIG. 1200 depicts an array of Light Emitting Diodes in reflective walled cups with an array of focusing/columniation lenses depicted.

FIG. 1300 depicts an array of Light Emitting Diodes in reflective walled cups with a single lens providing addition focusing/columniation.

FIG. 1400 depicts an array of focusing/columniation lenses placed over a single reflective wall cup.

FIG. 1500 depicts an array of large focusing/columniation lenses placed over an array of Light Emitting Diodes placed in reflective walled cups.

FIG. 1600 depicts an array of Light Emitting Diodes placed in single reflective wall cups sealed with a single optical, non-focusing/collimating window.

FIG. 1700 depicts an assembly of a Light Emitting Diode array, a heat transfer device (heat pipe) and a heat dissipating device (heat sink).

FIG. 1750 depicts an assembly with electrical connections where the heat transfer/heat sink assembly is also an integral electrical connection (anode).

FIG. 1800 depicts water cooling assembly for the Light Emitting Diode array.

FIG. 1850 depicts an assembly which first transfers the heat by way of heat pipe and then removes the heat by way of circulation water.

FIG. 1900 depicts a machinist drawing for constructing a Light Emitting Diode array for a Light Emitting Diode dental curing light source.

FIG. 1910 depicts a machinist drawing for constructing a Light Emitting Diode array for a Light Emitting Diode dental curing light source.

FIG. 1920 depicts a machinist drawing for constructing a Light Emitting Diode array for a Light Emitting Diode dental curing light source.

FIG. 1930 depicts a machinist drawing for constructing a Light Emitting Diode array for a Light Emitting Diode dental curing light source.

FIG. 1940 depicts a machinist drawing for constructing a Light Emitting Diode array for a Light Emitting Diode dental curing light source.

FIG. 2000 depicts a machinist drawing for constructing the heat sink (air) for a Light Emitting Diode dental curing light source.

FIG. 2010 depicts a machinist drawing for constructing the heat sink (air) for a Light Emitting Diode dental curing light source.

FIG. 2020 depicts a machinist drawing for constructing the heat sink (air) for a Light Emitting Diode dental curing light source.

FIG. 2030 depicts a machinist drawing for constructing the heat sink (air) for a Light Emitting Diode dental curing light source.

FIG. 2100 depicts and assembly drawing to assemble a Light Emitting Diode dental curing light source.

FIG. 2110 depicts an assembly drawing to assemble a Light Emitting Diode dental curing light source.

FIG. 2200 depicts an electrical schematic to construct a circuit which would modulate the Light Emitting Diode array of a Light Emitting Diode dental curing light source.

FIG. 2300 depicts an electrical schematic to construct a circuit which would drive the Light Emitting Diode array of a Light Emitting Diode dental curing light source.

FIG. 2400 depicts an electrical schematic to construct a circuit which would charge the batteries of and allow AC (plugged into the wall) operation of a Light Emitting Diode array of a Light Emitting Diode dental curing light source.

FIG. 2500 depicts an electrical schematic to construct the AC power supply for a Light Emitting Diode array for a Light Emitting Diode dental curing light source.

FIG. 2600 depicts an assembly drawing for the cooling layout of a Light Emitting Diode dental curing light source where the cooling is accomplished by water circulation or phase change heat effussion material.

FIG. 2700 depicts an assembly drawing for a Light Emitting Diode dental curing light source.

FIG. 2800 depicts and assembly drawing for a Light Emitting Diode dental curing light source.

FIG. 2900 depicts an assembly drawing for a Light Emitting Diode light source.

FIG. 3000 depicts an assembly drawing for a Light Emitting Diode light source.

X. DETAILED DESCRIPTION OF SOME EMBODIMENTS OF THE INVENTION

Figure 100:
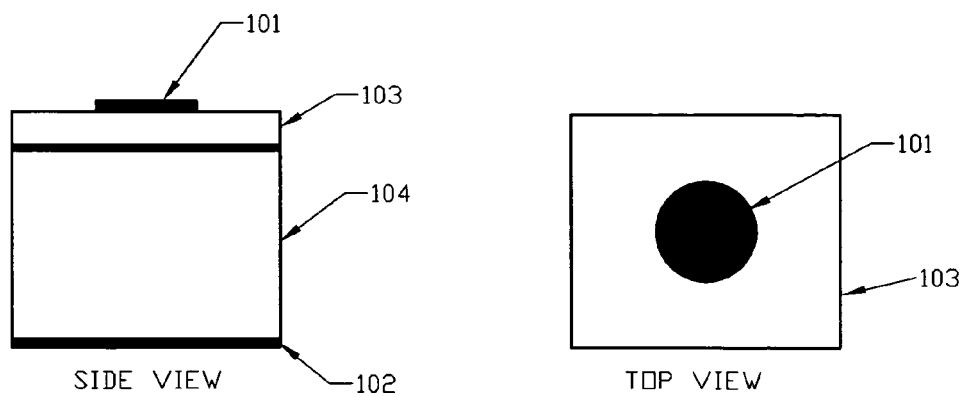
FIG. 100 depicts the side view and top view on a single Light Emitting Diode.

The invention first takes the LED as an electronic component without any lenses or wires attached, FIG. 100. The LED is essentially a cube with dimensions on the order of 0.250 millimeters, FIG. 100. On the top surface is an Anode (101). The bottom surface is metallized and serves as the Cathode and the heat transfer point/medium (102). The LED also contains a layer of semiconductor that is doped with specific materials in specific concentrations to produce the desired wavelength of light (103). Finally, the LED contains a layer of semiconductor substrate (104). When electrical current is passed between the cathode (102) and the anode (101), photons of a particular wavelength (depending on the composition of the materials) are emitted from the doped semiconductor layer (103).

Figure 200:
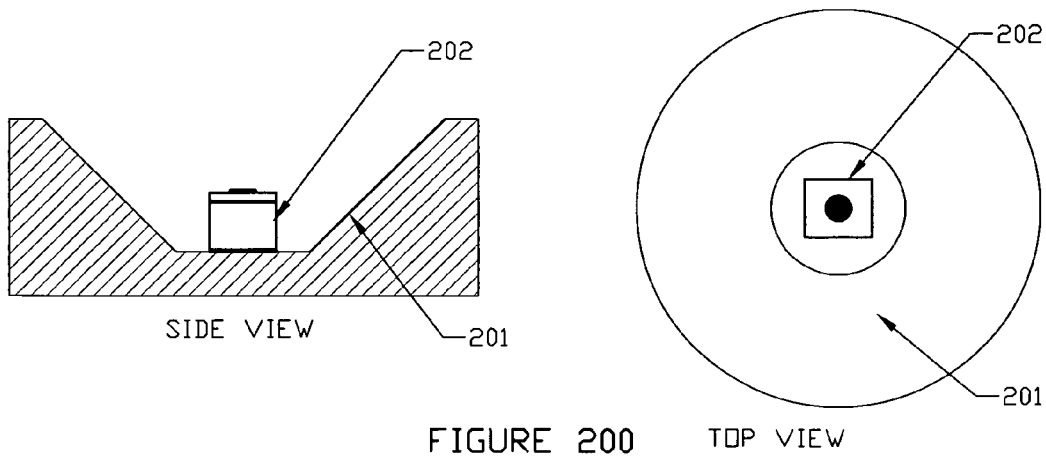
FIG. 200 depicts the side view and top view of a Light Emitting Diode placed in a reflective cup.
Figure 300:
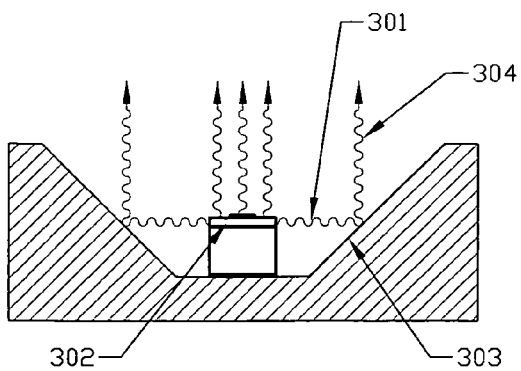
FIG. 300 depicts ideally light being emitted from the Light Emitting Diode and then being reflected by the reflective angled surfaces of a reflective cup.
Figure 400:
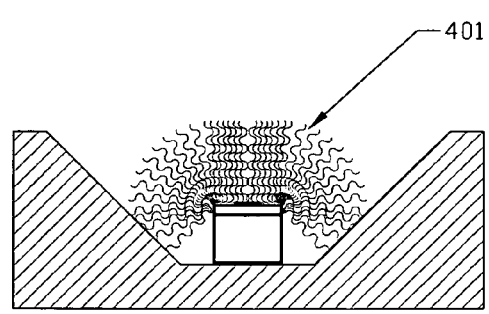
FIG. 400 depicts realistic light emission from a Light Emitting Diode.
Figure 500:
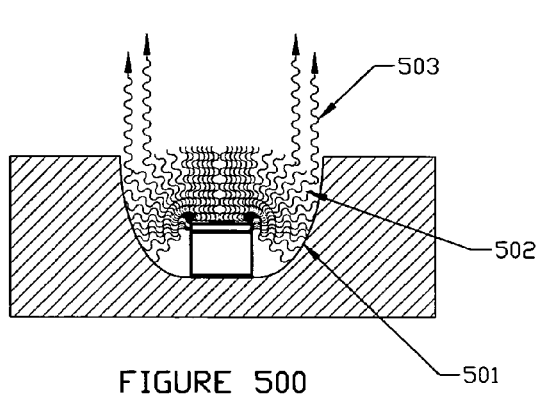
FIG. 500 depicts light being generated by a Light Emitting Diode and being reflected by a curved surface reflective cup.
Figure 600:
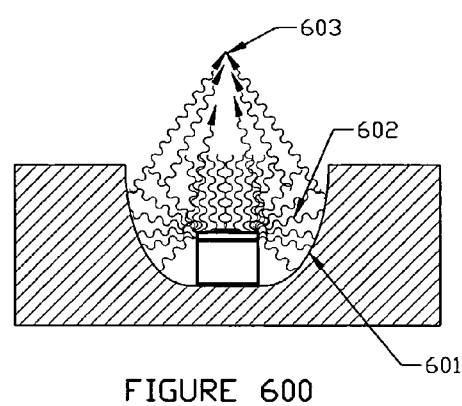
FIG. 600 depicts light being generated by a Light Emitting Diode and being reflected to a specific focal point from a curved surface reflective cup.
Figure 700:
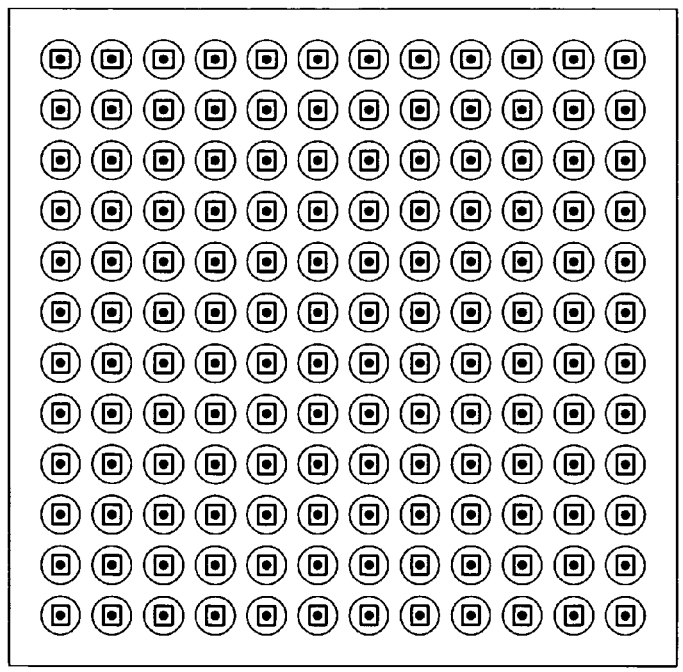
FIG. 700 depicts an array of 144 Light Emitting Diodes placed in 144 separate reflective cups.

Secondly the invention places the LED or LED array on one side of a flat substrate in all configurations of the invention the substrate is both electrically and thermally conductive. This provides the invention with two unique and superior feature; the heat is immediately removed from the LED and the heat removing/transporting substrate becomes integral with the anode of the LED hence serving as a heat removal device and electrical connection. It is also useful to the invention to place the individual LED into a reflective 'cup' which reflects the omnidirectional emitted photons into a single direction, FIG. 200. In the simplest of the invention's cup designs (200) the walls of the cup (201) are manufactured such that they are on a 45 degree angle. FIG. 300, for this design the photons are emitted, theoretically and idealistically, out of the top of the LED and in a horizontal plane (301) from the side of the semiconductor layers (302), the 45 degree side wall (303) would, theoretically and idealistically, reflect the emitted photon and redirect it in one direction 90 degrees from its origin (304). However, in practice, FIG. 400, LEDs emit photons (401) in all directions. The invention improves the efficiency of reflection by providing additional cup designs such as a cups containing hemispheric, elliptical or parabolic curve. FIG. 500, the elliptical cup (501), because of its curved surfaces reflects omnidirectional photons (502) into one directional photons (503). Furthermore, FIG. 600, by adjusting the altitude of the LED within the ellipse (601) the invention allows for the omnidirectional photons (602) to be reflected to a specific, predetermine, focal point in space (603). The engineer utilizes the well known optical equation 2/Radius=1/Focal Point+1/Optical Source to design hemispherical shaped cups and the well know optical equation $X^2=4PY$ to design Parabolic and Elliptical shaped cups. By engineering specific cup shapes and engineering specific placement of the LED within the cup, the invention allows the majority of photons produced by the LED to be placed at a specific point in space where they are needed. Additional cup designs that are useful to the invention (with or without the lenses illustrated) are illustrated in FIGS. 625, 650, and 675. The specific examples of cup design listed above are not intended to be restrictive to the invention in any way, for instance, a pyramidal (upside down) design as been suggested. The descriptions are simply given to illustrate the potential of specific cup designs. The actual design of the cups would be varied and specific to the application.

Figure 800:
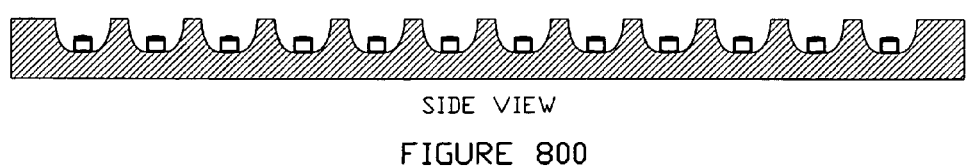
FIG. 800 depicts a side view of FIG. 700 depicting curved reflective surfaces of the individual cups.

Thirdly the invention assembles many LEDs into arrays in order to achieve higher optical output powers than are achieved with a single LED. FIG. 800, the invention provides for single LEDs placed in a many cup array. However, the invention is not restricted to this configuration. FIG. 900, in the invention the array can be accomplished by placing a number of LEDs within the same cup. Furthermore, the invention also utilized an array of LEDs in each cup coupled with and array of cups, FIG. 1000. In FIG. 1000 there are 4 single LEDs per cup and an array of 16 cups in a circular pattern. The invention is not limited to circular pattern arrays (1000) and square pattern arrays (800), indeed, the pattern of the array is only limited to the potential application. Furthermore, the description of single LEDs in a cup (800) or an array of 4 LEDs in a cup (900) is not meant to restrict the invention to these two descriptions, again, the number of LEDs arrayed per cup is only limited by the application to which it is intended. It is also useful to the invention to manufacture various shapes into which the cups are machined or stamped, FIG. 1100. In this configuration (1100) the invention takes advantage of the light reflecting design of the cup and further enhance these properties by positioning the cups themselves in a dish shaped plate. This illustration is not meant to restrict the usefulness of the invention to a flat shaped array of cups (800) and a dish shaped array of cups (1100), on the contrary, it is meant to illustrate the complexity that can be incorporated by the invention in order to suite the particular needs of an application. FIGS. 1125 and 1150 illustrate additional arrays and 'cup' configurations that are useful to the invention. FIG. 1125 illustrates array configuration in which many LEDs can be placed in arrays that are approximately ½ inch in diameter 1126, 1127, and 1128 are illustrations of cup designs that are in a 'trench' format, where the sides of the trench are designed in an angled or curved shape. FIG. 1150 illustrates array configurations win which many LEDs can be placed in arrays that are approximately 1.5 inches in diameter. 1151 utilizes the trench rather than individual cup design. Again these examples are not meant to be restrictive.

They are meant to illustrate some of the many potential array/cup designs that are useful to the invention.

Fourthly, the invention makes use of single lenses, including but not limited to Graded Index of Refraction (GRIN) lenses, lens arrays, including but not limited to Graded Index of Refraction (GRIN) lenses and holographic films, including but not limited to Graded Index of Refraction (GRIN) lenses in order to further process the light and deliver it, in its most useful quantities and qualities, to the specific applications. FIGS. 625, 650, 675, and 1200, the invention provides for the use of miniature lenses or holographic films (1201) placed directly over the individual cups (1202) forming an array of lenses or holographic films. FIG. 1300, the invention also allows for the use of a single lens or holographic film (1301) to be placed over the entire array of cups (1302). FIG. 1400, it is also useful to the invention to provide an array of lenses or holographic films (1401). The array of lenses or holographic films could contain many lenses, many films or a combination of lenses and films. Furthermore, it is useful to the invention to place these arrays over a single cup as illustrated in FIG. 1400 but it is also useful to the invention, FIG. 1500, to place a place an array of lenses (1501) and/or holographic film(s) over an array of cups (1502). Whether or not lenses or holographic films or arrays of lenses and/or holographic film(s) are used, it is useful to the invention to seal the LEDs, singularly or in an array, to protect them from environmental conditions that are adverse to their operation. FIG. 1600, an appropriate sized piece of anti-reflective (AR) coated optical glass (1601) is placed over the array (1602) and secured with ultraviolet light cured optical adhesive (1603) thus protecting the LEDs from adverse environmental conditions. The discussion and examples listed by way of lenses, holographic films and sealing windows (optical glass) are not intended to restrict the invention to the described scenarios but is rather to illustrate some of the many potential configurations that are useful to the invention. For instances, it has been suggested that micro ball lenses could be used for particular applications. The configuration of lenses, holographic films and sealing optics are only limited to the dictation's of the particular application.

Fifthly, the invention facilitates the removal thermal energy from single LEDs in a flat mounted configuration or in a single cup or from arrays of cups with single LEDs or from arrays of cups that individually contain arrays of LEDs while it maintains electrical insulation and conductivity where appropriate. Cup is defined in the context of this patent as a "shaped hole" in which a single LED or a number of LEDs can be placed. The word cup, as used in this invention, refers to any configuration that could accept an LED or LEDs. FIGS. 1120 and 1115 illustrate cups that are circular while FIGS. 1105, 1110 and 1130 illustrate cups that are formed in a 'trench' configuration. There is no shape constraints to the definition of cup in this invention, however, all cup designs have angled, curved, square or combinations of angled, curved or square walls designed to gather and reflect the photons produced by the LED toward the surface where the photons are needed. FIG. 1700, the cup housing may be manufactured from a thermally and electrically conductive material (substrate) such as copper and is plated with optically reflective, thermally conductive and electrically conductive material such as first nickel and then rhodium, or silver(1701). The LED(s) then may be secured to the bottom of the cup(s) using a thermally and electrically conductive adhesive such as silver filled epoxy (1702). The separate sections of LED/cups (1703) are then bonded to a plate made of heat conducting material (substrate) such as aluminum or copper (1710) with a space between the cup sections (1704) to provide electrical isolation. They are bonded to the plate using a thermally conductive but electrically insulating adhesive such as Thermal Epoxy, Electrically Insulating (1705). The LED(s) are then electrically connected by soldiering or conductively bonding the gold wires to the contacts (1706) and connecting them in series to the next electrically isolated cup(s) (1707). A gold wire is then soldiered or bonded to the contact of the last LED(s) (1708) in the series and is taken out to connect to the positive side of the direct current power source (1709). A gold wire is then soldiered or bonded to the cup material of the first LED(s) (1711) in the series and directed toward the negative side of the direct current power source (1712). Optical adhesive such as Ultra-Violet Activated Optical Adhesive is placed around the tops of the cups (1713), the gold wire leaving the last in the series of LED(s) is then embedded in the optical adhesive (1714) to provide electrical insulation. The optical window (or lenses, holographic films or arrays of lenses and/or holographic films and/or optical windows) (1715) is then position and set into the optical adhesive (1713) and the optical adhesive is cured with an ultra-violet light source. This assembly is then soldiered or bonded (using a thermally conductive adhesive) (1716) to a heat pipe (1717). The heat pipe is then soldiered or bonded to a heat sink (1718) manufactured from a thermally conductive material designed to dissipate heat in to a heat dissipation environment such as aluminum or copper. The heat dissipation environment is an environment that conducts the heat away from the heat sink such as air, water, phase change heat effusion material or a combination of air, water, and phase change heat effusion material. The heat sink is then secured to a chamber (1719) which houses either the direct current power supply, batteries to supply direct current or facilitates connection to an outside direct current power supply. This chamber is then connected to a fan (to move air, water and or phase change heat effusion material (1720) if additional cooling is requisite for the application. This discussion of configuration is not restrictive to the invention. Indeed, the usefulness of the invention for an application, in large part, is due to the inventions ability to be easily configured for specific applications. For instance it has been suggested that rather than having an electrically conductive plating placed on the cup material (1703) that an optically reflective plastic coating be used instead. In this configuration an electrically conductive substrate would be placed at the bottom of the cup (1702) between the cup and the LED(s), both being secured with electrically conductive epoxy. Another solution would be to mask the bottom of the cup before plastic coating then remove the mask and epoxy the LED in place as described earlier.

The LED(s) need not be wired completely in series. That is to say that you could build a pie shaped (square or round) device that has arrays of LEDs and cups in sections of the pie, FIG. 1000 illustrates such a scenario or configuration. In FIG. 1000 there are 4 sections which contain 4 cups each. Each cup contains 4 LEDs. In such a case the negative side of a direct current power source would be attached to one of the sections of cup material. The electrical connectors of each of the sixteen LEDs in this first section would have gold wires soldiered to them and each of these wire would then be soldiered to the next, or second, section of the cup material. The electrical connectors of each of the sixteen LEDs in this second section would have gold wires soldiered to them and each of these wires would then be soldiered to the next (third) section of the cup material. The electrical connectors of each of the sixteen LEDs in the third section would have gold wires soldiered to them and each of these wire would then be soldiered to the next (forth) section of the cup material. The electrical connectors of each of the sixteen LEDs in the forth section would have gold wires soldiered to them and each of these wire would then be directed to the positive side of the direct current power source. In effect and actually this would produce a series circuit which contains 4 series of 16 LEDs wired in parallel.

The substrate used to manufacture the cups (1703) may be made of the same material used to manufacture the substrate for heat removal (1710) making it an integral one piece assembly, refer to FIGS. 1910, 1920, 1930 and 1940. In this configuration the substrate is an integral heat sink. Electrical isolation is accomplished by bonding a copper conductive sheet using non-conductive epoxy to the top surface of the substrate and wire bonding the LEDs' cathodes to the copper conductive sheet, refer to FIG. 1930. In this electrical configuration the substrate conducts heat away from the LEDs while conducting electrical current to the anode, electrical current is supplied to the cathode by way of a sheet of copper that has been secured with non-conductive epoxy to the top of the substrate. Furthermore, the design of FIG. 1130 incorporates two electrical circuits (1133, 1135) which are electrically isolated by machined paths (1134, 1131). This allows two separate types of LEDs (for instance 430 nanometer and 450 nanometer) to be incorporated into the same curing device. This design is incorporated into the proto-type that was constructed and tested and is the subject of the example below.

Another configuration useful to the invention would eliminate the heat pipe and provide a heat dissipation environment directly in the substrate. Refer to FIG. 1800. 1801 is a heat dissipation environment chamber which allows the heat dissipation environment material (air, water, phase change heat effusion material, or combination thereof) to simple absorb the heat while being stored in the chamber or may be circulated through the chamber between port (1802, 1803). As is the configuration discussed above the substrates in this configuration can be separated as depicted or may be integral, made of the same material with no separation, providing heat removal, heat dissipation and integral anodic electrical connection. Yet another useful configuration would be to add the heat pipe, refer to FIG. 1850, to move the 'bulky' heat dissipation environment chamber away from the slender, light weight, array assembly. In this configuration heat is immediately transferred from the LEDs through the substrate (1851) (either separated or integral as discussed above), through the heat pipe (1852) and into the heat dissipation environment chamber (1853). The heat dissipation environment chamber (1853) which allows the heat dissipation environment material (air, water, phase change heat effusion material, or combination thereof) to simply absorb the heat while being stored in the chamber or may be circulated through the chamber between port (1854, 1855).

Another configuration would separate the cathode from the anode near the top or anode end of the LEDs. FIGS. 625, 650, and 675 Illustrate such a configuration. Where 626, 651, and 676 represent an thin film of electrically insulating material, 627, 652, and 677 represent a layer of electrically conductive material such as copper, or copper plated with gold, 628, 653, and 678 represent the wire that would attach the LEDs' anode to the electrically conductive layer. The cathode (629, 654, and 679) is then bonded directly to the heat sink material/configuration (630, 655, and 680) utilizing heat and electrically conductive adhesive producing a unique integral anode heat sink configuration. The circuits are then separated, where necessary, on the top electrically conductive layer (627, 652, and 677). FIG. 1128 illustrates 'trenches' (1131 and 1134) cut through the electrically conductive layer (627, 652, and 677) into the electrically insulating material (626, 651, and 676). This configuration (1130) effectively produces two, electrically separated circuits (1133 and 1135). This configuration allows to wire approximately ½ of the LEDs in parallel with each other and the other half of the LEDs in parallel with each other and then wire the halves in series, enabling the designer to manage voltage and current. It also allows the designer to operate two different types of LEDs that have different wavelength output and would require different currents and voltages to drive them optimally.

In some embodiments of the invention it is desired to modulate the light output in order to obtain prescribed post cure physical properties from the composite. For more information on how this accomplished see U.S. Pat. No. 6,008,264 which is hereby incorporated by reference.

EXAMPLE:

A LIGHT EMITTING DIODE DENTAL CURING LIGHT SOURCE

Obtain a ½ inch diameter by approximately 2 inches in length bar of alloy 110 copper from a source such as MSC Industrial Supply Co., Melville, N.Y. Obtain a piece of copper clad G10 PCB stock from a source such as Precision Technology, Salt Lake City, Utah. Cut a piece of the copper clad G10 approximately ¾ of an inch in diameter. Soldier the cut piece of G10 to the end of alloy 110 copper bar stock. Have a machine shop such as Axis Machine, Salt Lake City, Utah machine the assembly according to the specifications in FIGS. 1900, 1910, 1920, 1930, 1940. Take the machined assembly to a metal plating company such as Quality Plating Company, Salt Lake City, Utah and have the electrically plate the top conductive surface with gold according to mil spec G45204C. Further have them plate the reflective trenches with silver according to mil spec QQS365. Obtain 84-450 nanometer LEDs from Cree, Durham, N.C., Part Number: C450CB290E1000, 65-430 nanometer LEDs from Cree, Durham, N.C., Part Number: C430CB290E1200. Send the LEDs, FIG. 1910 and FIG. 1130 with instruction to set and wire bond the 430 nanometer LEDs to 1132 and the 450 nanometer LEDs using DM6030HK-SD/H569 Silver Filled Epoxy Paste (Diemat, Inc., Topsfield, Mass.) to a company like LDX Optronix, Maryville, Tenn. Have a machine shop such as Axis Machine, Salt Lake City, Utah construct a heat sink according to the specifications in FIGS. 2000, 2010, 2020, 2030. Obtain a ⅜ inch diameter by 6 inch length of heat pipe from a company such as Thermacore International Inc., Lancaser, Pa. (Part Number HP-1 0.375 X 6.0). Attach the heat pipe to the heat sink as illustrated in FIGS. 2100 and 2110 using DM6030HK-SD/H569 Silver Filled Epoxy Paste (Diemat, Inc., Topsfield, Mass.). Attach the LED array assembly completed by LDX Optronix to the other end of the heat pipe as illustrated in FIGS. 2100 and 2110. Have a machine shop such as Axis Machine construct a housing out of a plastic material in accordance with the illustration in FIGS. 2100 and 2110. Have a company such a KWM Electronics Corp., West Jordan, Utah manufacture 4 printed circuit according to the schematic specification in FIGS. 2200, 2300, 2400 and 2500. Install the circuits created from FIGS. 2200 and 2300 into the handle (2101 and 2102 respectively) as illustrated in FIG. 2100. Further install the circuit created from FIG. 2400 into the battery compartment (2103) as illustrated in FIG. 2100. The final circuit is mounted in a small kit box available from any Radio Shack, Nationwide. At household 120 volt AC input cord is installed and an output cord with the corresponding jack on the circuit produced by FIG. 2400 is also installed such that the output cord from the External Power Supply Assembly will plug into the circuit created by FIG. 2400 which is installed in the battery compartment. This enables the batteries to be recharged or the light to be operated off of household 120 volt AC while the batteries are being recharged. Obtain 8-AA Nickle Metal Hydride batteries from a company such as DigiKey, Theif River Falls, Minn. and install them in the battery compartment according to the illustration in FIG. 2100. Obtain a small 12 volt DC fan from a company such as DigiKey, Theif River Falls, Minn. and install the fan in the heat dissipation environment chamber (2105) as illustrated in FIG. 2100. The device does not necessarily have to have a fan. It could be run with natural air convection providing the cooling, water or a phase change heat effusion material such as sodium Sulfate Decahydrate, Aldrich Chemical Co., Milwaukee, Wis. In such a configuration the solid Sodium Sulfate Decahydrate would absorb the heat from the heat pipe and/or heat sink. As it absorbs the heat it converts from a solid to a liquid (phase change) storing the heat. The heat could then be removed by convection or by way of a mechanical linkage, possibly in a 'recharge station' which would convert the sodium Sulfate Decahydrate to a solid form again. Using any number of phase change hear effusion materials is very useful to the invention in that it eliminates the need for a fan which places additional current demand on the batteries and circuitry, it also adds the noise of the fan to the environment where the light is used. In a configuration where water provides the heat dissipation environment, water could even be stored in the chamber (2115) and re-circulated through the heat sink compartment, making the heat sink compartment and chamber 2115 the entire heat dissipation environment. Of course the water could be simply be pumped through the environment and discarded through an input and output port constructed in the chamber as well.

ADDITIONAL CONFIGURATION EXAMPLES

The basic concepts, designs, and circuitry of this example are not strictly limited to the design of placing the LED array in the immediate vicinity of the tooth. For instance it could be configured such that the LED array is placed in the main housing and the light is delivered by fiber optic or light guide as illustrated in FIG. 2600. The LED array (2602) is mounted to the end of a heat pipe (2606) which is then attached to a heat sink (2605), the heat sink being integrated also as the anode for the LEDs as described earlier. The Led Array (2602) produces light which passes through a lens, lens array or halographic film as discussed earlier. The light then passes into the light delivery device (2604) which could be a rigid light guide as portrayed in FIG. 2600 or could be a single fiber or a bundle of fibers. The fan compartment (2601) could be filled with water, a phase change heat effusion material as illustrated in FIG. 2600 and discussed earlier or it could contain a fan for cooling.

The basic concepts, designs, and circuitry of this example are certainly not limited to a certain configuration in housing design. FIG. 2700 illustrates another potential 'pistol' type design which incorporates the LED array close to the working surface while FIG. 2800 illustrates another potential 'pistol' type design which incorporates the LED array within the housing utilizing a light delivery device to get the light to the work surface.

The basic concepts, designs, and circuitry of this example are certainly not limited to an LED array of a certain size and for use in dentistry only. FIG. 2900 illustrates a 'pistol' type device that contains an LED array (2901) approximately 3 times the diameter of the example, which would contain approximately 5 times as many LEDs in the array. The LED array uses an integral anode/heat sink configuration where the heat sink (2903) may or may not include a heat pipe (2902). It contains a cooling compartment (2904) which could house a fan, nothing at all, water, or a phase change heat effusion material or a combination thereof. The heat dissipation environment could be stagnant or circulating. It contains a space for circuitry (1905) and for batteries (2906) and could be operated by the electronic presented in schematic detail earlier. A device such as the one illustrated in 2900 could designed for use as a dental curing light, dental bleach activator, forensic light source to name but a few.

The basic concepts, designs, and circuitry of this example need not be limited to 'pistol' type designs. FIG. 3000 illustrates the ability of the concepts to be incorporated in a 'flashlight' design which contains all of the basic elements of the invention: an LED array (3001), with or without a lens, lens array, halographic film, light delivery device or combination thereof, a heat sink (3003) which could or could not also be the anode, the heat sink may or may not incorporate a heat pipe (3003), the housing includes a space for electronic (3005), batteries (3005), and a cooling compartment (3007).

None of the overall designs necessarily have to have a battery compartment. The invention could be run completely on AC power.

The foregoing description and drawings are illustrative of preferred embodiments of the invention and are not intended to be limiting of the invention's scope. The scope of the invention is defined by the appended claims, which should be interpreted to cover that which is disclosed herein and equivalents thereof.

What is claimed is:

1. An apparatus configured as a light emitting diode dental curing light source for curing composite materials, said apparatus comprising:
    a) a plurality of light emitting diodes being capable of emitting light when supplied with adequate electrical current, each of the plurality of light emitting diodes having a bottom surface configured as a heat transfer surface;
    b) a first substrate portion upon which the bottom surface of each of said plurality of light emitting diodes are mounted, said first substrate portion being electrically conductive and thermally conductive;
    c) a second substrate portion thermally connected to the first substrate portion, said second substrate portion being thermally conductive and electrically insulating;
    d) a heat pipe capable of transferring heat from one location to another, said heat pipe having a first end portion and a second end portion, said first end portion being thermally connected to the second substrate portion;
    e) a heat sink constructed of a material capable of dissipating heat into a heat dissipation environment, said heat sink being thermally coupled to the second end portion of the heat pipe; and
    f) control circuitry capable of controlling electrical current transmission to said plurality of light emitting diodes in order to control light production by said plurality of light emitting diodes; wherein heat generated by the plurality of light emitting diodes is transmitted to the heat sink via the first substrate portion, the second substrate portion and the heat pipe.

2. The apparatus according to claim 1, wherein the first substrate portion is configured with a plurality of cups therein, at least some of the cups being sized and configured to have one or more light emitting diodes positioned therein.

3. The apparatus according to claim 2, wherein each of the plurality of cups have angled walls, curved walls, square walls or a combination thereof.

4. The apparatus according to claim 2, wherein the plurality of cups are formed in a dish shape.

5. The apparatus according to claim 2, wherein the first substrate portion is configured with one or more trenches therein.

6. The apparatus according to claim 2, wherein at least some of the cups being sized and configured to have multiple light emitting diodes positioned therein.

7. The apparatus according to claim 2, wherein the plurality of cups are machined or stamped.

8. The apparatus according to claim 2, wherein one or more of the plurality of cups have a shape selected from the group comprising, parabolic, elliptical, hemispherical and pyramidal.

9. The apparatus according to claim 2, wherein one or more of the plurality of cups have a shape configured to reflect the emitted light to a specific focal point.

10. The apparatus according to claim 1, wherein the bottom surface is further configured as an electrical contact surface.

11. The apparatus according to claim 1, comprising a plurality of first substrate portions, each of said plurality of first substrate portions having one or more light emitting diodes mounted thereon, said plurality of first substrate portions connected to the second substrate portion.

12. The apparatus according to claim 1, further comprising an optical element optically coupled to the plurality of light emitting diodes.

13. The apparatus according to claim 12, wherein the optical element is selected from the group comprising a lens, a holographic film, an array of lenses, an array of lenses and holographic films, an array of holographic films, a graded refractive index lens, an array of graded refractive index lenses, an optical window and an array of optical windows.

14. The apparatus according to claim 1, wherein the first substrate portion is coated with an optically reflective material.

15. The apparatus according to claim 1, wherein the plurality of light emitting diodes are comprised of light emitting diodes of different wavelengths.

16. The apparatus according to claim 1, wherein the first substrate portion has a top surface and wherein the top surface is a copper sheet.

17. The apparatus according to claim 16, wherein the copper sheet is divided into electrically isolated portions, wherein each electrically isolated portion has one or more light emitting diodes mounted thereon.

18. The apparatus according to claim 1, wherein the plurality of light emitting diodes are optically coupled to a light guide or a single optical fiber or a bundle of optical fibers.

19. The apparatus according to claim 1, wherein the heat sink is cooled by one or a combination of air, water and a phase change heat transfer material.

20. The apparatus according to claim 1, wherein the first substrate portion is configured with one or more trenches therein.

* * * * *